US012708674B2

(12) United States Patent
Ayyala et al.

(10) Patent No.: US 12,708,674 B2
(45) Date of Patent: Aug. 18, 2026

(54) METHODS AND COMPOSITIONS FOR DELIVERY OF A THERAPEUTIC AGENT

(71) Applicants: Ramesh S. Ayyala, Tampla, FL (US); Nurettin Sahiner, Tampa, FL (US)

(72) Inventors: Ramesh S. Ayyala, Tampla, FL (US); Nurettin Sahiner, Tampa, FL (US)

( * ) Notice: Subject to any disclaimer, the term of this patent is extended or adjusted under 35 U.S.C. 154(b) by 766 days.

(21) Appl. No.: 17/087,508

(22) PCT Filed: Mar. 28, 2019

(86) PCT No.: PCT/US2019/024549
§ 371 (c)(1),
(2) Date: Nov. 2, 2020

(87) PCT Pub. No.: WO2019/191405
PCT Pub. Date: Oct. 3, 2019

(65) Prior Publication Data

US 2021/0260213 A1 Aug. 26, 2021

Related U.S. Application Data

(60) Provisional application No. 62/650,209, filed on Mar. 29, 2018.

(51) Int. Cl.

| | |
|---|---|
| ***A61K 47/69*** | (2017.01) |
| ***A61K 31/407*** | (2006.01) |
| ***A61K 31/496*** | (2006.01) |
| ***A61K 31/513*** | (2006.01) |
| ***A61K 38/14*** | (2006.01) |
| ***A61K 45/06*** | (2006.01) |

(52) U.S. Cl.
CPC ........ *A61K 47/6939* (2017.08); *A61K 31/407* (2013.01); *A61K 31/496* (2013.01); *A61K 31/513* (2013.01); *A61K 38/14* (2013.01); *A61K 45/06* (2013.01)

(58) Field of Classification Search
CPC .... A61L 2/10; A61L 2202/11; A61L 2202/20; A61L 2202/14
See application file for complete search history.

(56) References Cited

U.S. PATENT DOCUMENTS

2012/0095206 A1 4/2012 Tor-Chern

FOREIGN PATENT DOCUMENTS

WO WO/2000/046252 A1 8/2000
WO WO2014/181141 A1 11/2014

OTHER PUBLICATIONS

Study on the Preparation and Performance of Cross-Linked Hyaluronic Acid Release Carrier, World Congress on Medical Physiics and Biomedical Engineering May 26-31, 2012, Beijing, China, vol. 33 of the series IFMBE Proceedinigs pp. 122-125. (Abstract).
Porous and modified HA particles as potential drug delivery systems, Nurettin Sahiner et al., Microporous and Mesoporous Materials, 155 (2012) 124-130.
Poly(sucrose) micro particles preparation and their use as biomaterials, Nurretin Sahiner et al., International Journal of Biological Macromolecules 66 (2014) 236-244.
One step preparation of polymeric maltitol particles, from a sugar molecule, maltitol for biomedical applications, Nurretin Sahiner, Materials Science & Engineering C 89 (2018) 205-212.
Mesoporous, degradable hyaluronic acid microparticles for sustainable drug delivery application, Nurretin Sahiner et al., Colloids and Surfaces B: Biointerfaces 177 (2019) 284-293.
Hyaluronic Acid Nanoporous Microparticles with Long In Vivo Joint Residence Time and Sustained Release, Palmieri et al., Part. Part. Syst. Charact. 2017, 34, 1600411.
Hyaluronic Acid and hyaluronic acid: Sucrose nanogels for hydrophobic cancer drug delivery, Suner et al., International Journal of Biological Macromolecules 126 (2019) 1150-1157.
Hyaluronic acid hydrogel particles with tunable charges as potential drug delivery devices, Ekici et al., Carbohydrate Polymers 84 (2011) 1306-1313.
The role of hyaluronic acid inclusion on the energetics of encapsulation and release of a protein molecule from chitosan-based nanoparticles, Al-Qadi et al., Colloids and Surfaces B: Bioiniterfaces 141 (2016) 223-232.
Colloidal drug carries from (sub)micron hyaluronic acid hydrogel particles with tunable properties for biomedical applications, Ilgin et al., Carbohydrate Polymers 82 (2010) 997-1003.
International Search Report for PCT Application PCT/US19/24549.
Written Opinion for PCT Application PCT/US19/24549.

*Primary Examiner* — Jessica Worsham
(74) *Attorney, Agent, or Firm* — Nolan Heimann LLP; Adam Diament

(57) ABSTRACT

Compositions of hyaluronic acid (HA) conjugated with antibiotics are disclosed for a rapid release antibiotic delivery system into a closed space to achieve rapid therapeutic range within 24 hours and effective elimination of the antibiotic within 80-120 hours. In particular, this invention is directed to compositions, method of preparation, and method of treatment to prevent invention using porous and non-porous embodiments of hyaluronic acid polymer conjugated with antibiotics or other therapeutic agents for rapid therapeutic delivery and controlled reduction of therapeutic dosages of antibiotics to prevent invention and reduce antibiotic resistance. Low concentration of crosslinkers conjugated with HA as well as using porogens and functional group modifiers allow other therapeutic to be conjugated to HA such as sugars and steroids. Suspension of HA conjugates in chitosan enable additional treatment means. Anticancer therapeutic agents may also be conjugated for controlled release using this system.

11 Claims, 16 Drawing Sheets

LinearHA

TMPGDE

GDE

Glycerol diglycidyl ether (GDE)

trimethylolpropane triglycidyl ether (TMP)

HA particles

Sodium trimetaphosphate (STMP)

poly(ethylene glycol) diglycidyl ether (PEGGE)

Hyaluronic acid (HA)

O O F OH N HN N

Ciprofloxacin

FIG. 5A

METHODS AND COMPOSITIONS FOR DELIVERY OF A THERAPEUTIC AGENT

CROSS-REFERENCE TO RELATED APPLICATIONS

This application is a national stage application, filed under 35 U.S.C. § 371, of International Application No. PCT/US2019/024549, filed Mar. 28, 2019, which claims benefit of U.S. Provisional Patent Application No. 62/650,209, filed Mar. 29, 2018, the contents of each are incorporated by reference in their entireties.

FEDERALLY SPONSORED RESEARCH OR DEVELOPMENT

None.

FIELD OF THE DISCLOSURE

The present invention relates to methods and compositions for delivery of a therapeutic agent, and more specifically, to a controlled antibiotic (or other drug) release, method of preparation, and method treatment using hyaluronic acid conjugated with an antibiotic or other therapeutic agent.

BACKGROUND OF THE INVENTION

Infection is the most important morbidity that the patient faces in the postoperative period. Most infections occur in the immediate postoperative period. In most of these cases, the source of infection is mostly bacteria from the patient's own skin. This is especially crucial in patients undergoing high risk prosthetic surgery, such as joint, spine and ocular surgeries. In all these locations, hardware is routinely placed into the human body. Examples include knee replacement, spinal fusion with screws/plate and intraocular lens. Procedures such as arthroscopy are also at high risk of infection. Acute colitis is another situation where local delivery of antibiotics may be curative.

In all these situations, once bacteria contact the prosthesis, it is very difficult to treat the infection unless the prosthesis is removed. The prophylactic usage of antibiotics during the peri and immediate postoperative period could potentially prevent acute postoperative infections. However, routine use of prophylactic antibiotics could potentially breed antibiotic resistant bacteria.

Hyaluronic acid (HA) has been used an application for a carrier of drug delivery. Hyaluronic acid has good biocompatibility, biodegradability, and nonimmunogenicity. It is a linear macromolecular mucopolysaccharide that is composed of alternating linked two saccharide units of glucuronic acid and N-acetylglucosamine. In addition, some groups of HA such as hydroxyl, carboxyl, and N-acetyl are suitable for chemical modification. HA and derivatives can act as drug carriers, sustained release, transdermal absorption, and improve drug targeting. For example, several dosing type systems have been used using HA acid, such as HA-methylcellulose hydrogel with alpha-Chymotrypsin, HA-microspheres, HA-aminoethyl iso-butylenate nanogel, and thiolated HA microhydrogels.

U.S. patent application Ser. No. 12/808,737 to Malle describes methods of producing crosslinked HA microbeads using divinyl sulfone (DVS), which can be useful as a delivery for pharmaceutical drugs, as bioactives in themselves, and as constituents in compositions in a wide range of biomedical applications. However, the ratio of HA to DVS is between 1:1 and 100:1 in dry weight of HA:DVS.

In particular surgical applications, maintaining a specified amount of drugs in a target location is difficult, such as in the eye. Various compositions and methods of treatment to prevent infection have been proposed. One such composition and method is disclosed in International Application PCT/US2008/076837 to Edelman et al., where a pharmaceutical composition for intraocular use was admixed with a biodegradable polymer, such as HA, extended a medicant therapeutic levels up to 30 days.

Another HA drug delivery system is disclosed in International Application No. PCT/SG2013/000389 to Venkatraman et al. It discloses use of an HA hydrogel to deliver drugs such as small molecules in a controlled manner, and for particular use in ophthalmology and dermatological conditions. The hydrogel comprises loaded vesicles dispersed in the HA hydrogel wherein the vesicles are loaded with one or more drugs and provide a sustained release of drugs conjugated with HA.

Yet another HA drug delivery system is disclosed in International Application No. PCT/US2013/022250 to Berkland et al. It discloses an HA particle comprising a plurality of free polymer chains extending from a surface of the particles such that the polymer chains are capable of association with polymers or with polymer chains on a surface of other particles.

Others have disclosed a one-step synthesis of HA to create hydrogel particles. (One-Step Synthesis of Hyaluronic Acid-Based (Sub)micron Hydrogel Particles: Process Optimization and Preliminary Characterization, Turk J Chem 32 (2008), 397-409, Sahiner and Jia). Drug carriers using colloids from submicron HA hydrogels have been made to have tunable properties for biomedical applications. (Colloidal drug carries from (sub)micron hyaluronic acid hydrogel particles with tunable properties for biomedical applications, Carbohydrate Polymers, Volume 82, Issue 3, 15 Oct. 2010, Pages 997-1003, Ilgin et al.). Crosslinking with HA has accomplished by several others, where HA as a drug delivery device. (See Structural Analysis and Mechanical Characterization of Hyaluronic Acid-Based Doubly Cross-Linked Networks, Macromolecules 2009, 42, 537-546, Jha et al.; Hyaluronic acid hydrogel particles with tunable charges as potential drug delivery devices Carbohydrate Polymers, Volume 84, Issue 4, 2 Apr. 2011, Pages 1306-1313). In addition, U.S. Patent Pub. No. 20100311963 discloses crosslinked HA in an emulsion to produce cross-linked hyaluronic acid and microbeads.

In addition to standard HA particles, porous and modified HA particles have been proposed as a potential drug delivery system. Sahiner at et al. report the utilization of silica particle preparation prior to HA particle preparation in the same microemulsion system, followed the removal of silica particles, and thereafter microporous HA particle were obtained. (Porous and modified HA particles as potential drug delivery systems, Microporous and Mesoporous Materials 155 (2012) 124-130, Sahiner et al.). Additionally, uniform size HA particle with nano porous morphology has been reported by Graziana Palmieri et al., using concomitant cross-linking of HA and crosslinking agent precipitations. (Hyaluronic Acid Nanoporous Particles with Long in vivo Joint Residence Time and Sustained Release, Particle & Particle System Characterization, 2017, 34, 1600411). In this study, an aqueous solution of bis-carbonylimidizine was used as crosslinker mixed with 1% weight/volume HA solution, and after shaking overnight, nanoporous HA particles were formed by precipitation of a viscous and high molecular weight HA solution induced by intra- and inter-molecular crosslinking.

Despite progress made in creating delivery systems, current uses of HA have a limit on the number of drugs or other compositions that can be bound to HA, thus limiting the potential of HA as a drug delivery system. Due to at least the above described shortcomings, there remains a continuing need for improved drug delivery systems.

All patent applications, patents, and non-patent literature cited in any part of this application are hereby incorporated by reference in their entireties for all purposes.

BRIEF SUMMARY OF THE PRESENT INVENTION

One strategy that could overcome some of the disadvantages presently used to deliver drugs to target regions, especially in surgical contexts, is to use a rapid release drug delivery system where an antibiotic, drug, other therapeutic agent is conjugated to HA, where the HA that releases the drug soon after delivery into a closed space (e.g., joint or meningeal space). Soon after delivery, the drug rapidly achieves therapeutic range, and by a predetermined time, such as between 48 and 72 hours, the conjugated drug is completely or nearly completely released from HA into the system. In the context of antibiotics, this strategy kills bacteria that have entered the surgical field as a contaminant. An advantage of this drug delivery system is that since the antibiotic is only system only for up to approximately 72 hours, the risk of development of resistant bacteria is minimized.

Common bacteria encountered in these surgical settings include gram-positive bacteria such as *Staphylococcus* and *Streptococcus*, but sometimes gram-negative bacteria such as *Pseudomonas*. While many types of antibiotics can be conjugated to HA for delivery, in preferred embodiments include conjugation of Vancomycin and Ciprofloxacin with HA. It should be noted that although the description may specify the conjugate with HA as an antibiotic, the conjugate maybe any type of therapeutic agent besides antibiotics, without detracting from the spirit of the invention.

There are several ways that drug delivery can be improved using HA, with the goal of having a delivery system that is capable of releasing the therapeutic agent (such as a drug or other antibiotic) soon after delivery into a closed space (for example, an eye, joint, meningeal space, etc.), which can achieve therapeutic range within 24 hours and be unconjugated and released from HA within 80-120 hours.

In a general sense, the HA, and HA modified systems use a rapid release delivery mechanism is capable of being tailored to release a therapeutic agent for a predetermined amount of time. For example, antibiotics can be released at a therapeutic dose into an eye for 72 hours, following injection of a slow release antibiotic. The delivery system can use specific crosslinkers that facilitate better biocompatibility, better swelling ability, faster degrading ability to produce a softer and more flexible end product that is easier or inject using a 27 G needle.

Specific crosslinkers may include glycerol diglycidyl ether (GDE), poly(ethylene glycol) diglycidyl ether (PEGGE), trimethylolpropane triglycidyl ether (TMPGDE), and sodium trimetaphosphate (STMP) with various amounts (e.g. from 50 and 200 mole % relative to HA repeating units) in the preparation of the HA drug delivery systems. These potential crosslinkers are depicted in FIGS. 1 and 2 for structures and images of crosslinkers.

To increase the number of therapeutic agents that be conjugated or otherwise delivered via HA, modifications of the HA particles may include generation of new functional groups, specifically —OH, —$NH_2$, —$SO_3H$, —COOH, —CN and —$PO_3H$, —R (alkyl and aryl groups), such that these new functional groups can be further used for increased antibiotic drug loading and/or conjugations with therapeutic agents. These functional groups, extending from crosslinkers, and/or modifying agents, can provide additional physical and chemical properties to the HA particles. In particular, —OH functional groups on HA can be used to conjugate antibiotics to help modify the drug release rate. Specific modifications to HA conjugated with antibiotic can delay the release profile of the system three to five days. A more rapid delivery can be accomplished by suspending HA in an antibiotic solution, which can increase the release profile to within 24 hours.

HA particles can also bind more than one drug simultaneously, thus becoming a multiple drug carrier, and can be created to release specific drugs during specific timeframes by choosing the appropriate crosslinker at a specific percent with various porogens and/or suspension mediums. For example, therapeutic agents can be released from the suspension at one rate (such as from zero to five days) and have a second release later (such as between two to five days) from the conjugation portion. For example, in addition to conjugating antibiotics to HA particles, steroids can further be conjugated that may have a release rate that lasts as long or longer than 14 days, while the antibiotic will only last five days.

One modification that can increase HA particle's ability to bind drugs is by the addition of sucrose (or other simple carbohydrate such as, but not limited to maltose, lactose, monosaccharides, disaccharides, sorbitol or other sugar alcohols), which can increase the ability to bind antibiotics or other drugs 10-fold, compared to HA without sucrose. The HA-sucrose conjugates also help attract bacteria to the modified HA-antibiotic conjugate to facilitate more rapid infection treatment.

In another aspect, a suspension of the HA-antibiotic is prepared in a suspension of a natural polymer, such as chitosan. The chitosan solution increases the ability of the HA-antibiotic to adhere to operative site surfaces, such as mucus membranes and epidermis, and can be applied with a spray or other means to deliver to target areas.

In other aspects a porous HA particle is created by using low concentration of divinyl sulfone (DVS) crosslinker (e.g. less than 20%) and porogen materials such as polyvinyl pyrrolidone (PVP), poly(vinyl alcohol) (PVA) and polyethylene glycol dimethyl ether (PEG) to increase the surface area available to link various drugs such as antibiotics. These HA particles can be modified to have various functional groups to conjugate various medicants, and in addition, to control the release rate of drugs in the conjugation, the pore size in the porous HA particles can be varied.

Another aspect of the present invention uses the efficacy of known antibiotic delivery systems by using porous HA, which allows for increased antibiotic conjugation to HA compared to non-porous embodiments of HA. The porous HA polymer increases the surface area, thereby increasing the number conjugation sites of therapeutic agents.

In one aspect of the present invention, use of a crosslinking agent such as DVS less than 10%, and more 10% with porogens such as PVP, PVA and PEG during microemulsion polymerization obtain porous HA particles.

In another aspect of the present invention, chemical modification to HA increases surface functionality to attach addition —OH, —$SO_3H$, —$NH_2$, —SH, —COOH, —CN, and —R (alkyl and aryl groups) or other functional groups to increase drug conjugation and additional physicochemical properties to HA particles.

In another aspect of the present invention, chemical modification to HA particles increases surface functionality to attach addition alky halides such as bromo- or chloro-alkanes with different alkyl chain lengths such as $Br(CH_2)_nCH_3$ where n can be 1 to 17 to increase hydrophobicity of HA particles to increase the hydrophobic drug loading capacity.

In yet another aspect of the present invention, a sugar, such as for example, sucrose, fructose, galactose, maltose, lactose, maltitol, sorbitol and their D- or L-forms can be conjugated during synthesis of the HA particle to attract bacterial to increase the antibacterial properties of the antibiotic conjugated HA particles.

In yet another aspect of the present invention, porous HA particle chemically modified or non-modified can be used for delivery of cancer medications such as, but not limited to, Mitomycin C, 5-Fluorouacil and Cisplatin.

In yet another aspect of the present invention, the therapeutic agent conjugated HA particle is either porous or non-porous, and conjugated with an antibiotic and chitosan, the chitosan thereby forming a viscous composition capable of adhering or forming a layer upon tissue surfaces to increase delivery of antibiotics to a target area. Such compositions may especially be useful for use in the eye, and during eye surgery, such as cataract surgery.

In yet another aspect of the present invention, HA may be conjugated with steroids such as dexamethasone, prednisolone, and triamcinolone, in combination with antibiotics and/or sugars, thereby providing a dual antibiotic and steroid delivery system.

In one general aspect there is a method of preparing a biologically active rapid release therapeutic agent polymer, the method comprising: (a) providing an alkaline solution of hyaluronic acid (HA), or a salt thereof, having HA repeating units; (b) providing a simple carbohydrate solution prepared in approximately a same mole ratio of the HA repeating unit of step (a); (c) mixing at least a portion of the solution of step (a) and the solution of step (b) together into solution, (d) mixing the solution of step (c) with a solution of AOT; (e) mixing the solution of step (d) with a crosslinking agent; (f) agitating for a sufficient time and at a sufficient temperature the solution of step (e) to produce HA particles thereby creating crosslinked HA repeating units and the simple carbohydrate; (g) precipitating the solution of step (f) HA particles; (h) mixing a therapeutic agent solution with the HA particles of step (g), wherein the therapeutic agent solution comprises a therapeutic agent, thereby forming an HA-carbohydrate-therapeutic agent conjugate.

In another aspect of the method above, the alkaline solution is NaOH, the simple carbohydrate is sucrose, the therapeutic agent solution is an antibiotic solution comprising an antibiotic, thereby forming an AH-carbohydrate-antibiotic conjugate, and wherein the crosslinking agent is at least one of glycerol diglycidyl ether (GDE), trimethylolpropane triglycidyl ether (TMPGDE), sodium trimetaphosphate (STMP), and divinyl sulfone (DVS), and is at a concentration of approximately 50 to 200 mole percent relative to HA repeating units.

In other aspects, the antibiotic solution is mixed with the HA particles for a predetermined amount of time at a predetermined temperature, and in some embodiments, for 24 hours at 80° C.

In other aspects there are additional steps of providing a chitosan solution and suspending the HA-therapeutic agent in the chitosan solution, thereby creating a viscous solution capable forming a viscous layer upon a target tissue surface, and the chitosan may be dissolved in acetic acid and water.

The method may also include providing a steroid solution having at least one steroid and mixing the steroid solution with the HA-carbohydrate-therapeutic agent conjugate to conjugate the steroid, thereby forming an HA-carbohydrate-therapeutic agent-steroid conjugate.

In other general aspect there is another method of preparing a biologically active rapid release therapeutic agent polymer, the method comprising: (a) providing an alkaline solution of hyaluronic acid (HA), or a salt thereof, having HA repeating units; (b) providing a solution of crosslinking agent wherein the crosslinking agent is at a ratio of between 1 percent mole and 20 percent mole relative to the HA repeating unit; (c) mixing the solutions of steps (a) and (b), thereby forming crosslinked HA particles; (d) precipitating the crosslinked particles formed in step (c) using a precipitating agent; and, (e) mixing a therapeutic agent solution with the HA particles, wherein the therapeutic agent solution comprises a therapeutic agent, thereby forming an HA-therapeutic agent conjugate. The therapeutic agent solution can be an antibiotic solution, thereby forming an HA-antibiotic conjugate. The crosslinking agent may be divinyl sulfone (DVS). The ratio of the crosslinking agent may be between 1 percent mole and 10 percent mole relative to the HA repeating unit, or may bet between 1 percent mole the 5 percent mole, or between 1 percent mole and 2.5 percent mole relative to the HA repeating unit.

Additional steps may be provided to modify groups on the HA-therapeutic agent conjugate by providing a solution of at least one of trimethylolpropane triglycidyl ether (TMPGDE), 3-chloro-2-hydroxy-1-propanesulfonic acid, 4-bromo butyronitrile, bromoacetic acid, tris(2-aminoethyl) amine, cysteamine, and bromo- or chloro-alkanes, wherein the bromo-alkane is characterized has having a formula of $Br(CH_2)_nCH_3$, wherein n is between 1 and 17, and the chloro-alkane is 3-chloropropylamine; and, suspending the porous-HA particles in the solution of thereby introducing at least one of —OH, —$SO_3H$, —CN, —COOH, —$NH_2$, —SH, and R functional groups for conjugate attachment.

Still additional steps may include providing a steroid solution having at least one steroid; and, mixing the steroid solution with the HA-antibiotic conjugate to conjugate the steroid, thereby forming an HA-antibiotic-steroid conjugate.

In yet another general aspect there is an additional method of preparing a biologically active rapid release therapeutic agent polymer, the method comprising: (a) providing an alkaline solution of hyaluronic acid (HA), or a salt thereof, having HA repeating units; (b) providing a solution of crosslinking agent wherein the crosslinking agent is at a ratio of between 50 percent mole and 100 percent mole relative to the HA repeating unit; (c) providing a solution of a porogen agent wherein the porogen agent is at a ratio of between 25 percent weight of HA and 50 percent weight of—HA—; (d) mixing the solutions of steps (a) and (b) and (c); (e) precipitating particles formed in step (d) using a precipitating agent; thereby forming porous-HA particles having an average surface area between approximately 21 $m^2/g$ to 0.014 $m^2/g$, an average pore volume of between approximately 11 $cm^3$/g and 1 $cm^3$/g and an average pore size of approximately 7 nm to 13 nm.

The crosslinking agent may be divinyl sulfone (DVS) and the porogen is selected from a group consisting of polyvinylpyrrolidone (PVP), Polyvinyl alcohol (PVA) and polyethylene glycol dimethyl ether (PEG).

Further steps include providing a solution of a therapeutic agent having a therapeutic agent; and, mixing the solution of the therapeutic agent with the porous-HA particles, thereby conjugating the therapeutic agent with the porous-HA particles. The therapeutic agent may be an antibiotic, and specifically may be Ciprofloxacin and Vancomycin. Modifications to create functional groups capable of bonding various molecules may be possible by providing a solution of at least one of trimethylolpropane triglycidyl ether (TMPGDE), 3-chloro-2-hydroxy-1-propanesulfonic acid, and 3-chloropropylamine; and suspending the porous-HA particles in the solution of at least one of trimethylolpropane triglycidyl ether (TMPGDE), 3-chloro-2-hydroxy-1-propanesulfonic acid, and 3-chloropropylamine, thereby introducing at least one of —OH, —$SO_3H$ and —$NH_2$ functional groups for conjugate attachment.

Additional steps include providing a steroid solution having at least one steroid; and, mixing the steroid solution with the HA-therapeutic agent conjugate to conjugate the steroid, thereby forming an HA-therapeutic agent-steroid conjugate. To include additional binding sites further steps may include providing a simple carbohydrate solution having a simple carbohydrate and mixing the simple carbohydrate solution with the porous-HA particles thereby forming at least one of a porous HA-carbohydrate-therapeutic agent conjugate and a porous HA-carbohydrate-therapeutic agent-steroid conjugate.

In another general aspect there is a biologically active rapid release therapeutic agent polymer composition comprising a hyaluronic acid (HA) polymer formed of HA repeating units, a therapeutic agent covalently bound to the HA polymer, a crosslinking agent having a ratio of less than 1:5 relative to the HA repeating polymer units, wherein the HA particles have an average surface area between approximately 22 $m^2$/g to 0.3 $m^2$/g, an average pore volume of between approximately 5 $cm^3$/g and 0.8 $cm^3$/g and an average pore size of approximately 5 nm to 8 num. The composition can rapidly release a therapeutic agent to achieve a therapeutic range within approximately 24 hours and the antibiotic is substantially released from the HA polymer within approximately 80-120 hours after administration, thereby preventing infection and limiting the occurrence of antibiotic resistance after rapid release of the antibiotic from the HA polymer. The therapeutic composition can be an antibiotic, the crosslinker can be divinyl sulfone (DVS), the ratio of crosslinking ratio may be less than 1:5, 1:10, 1:20, or 1:40 relative to the HA repeating unit. The HA polymer may be conjugated to a simple carbohydrate such as sucrose and the HA repeating units may be modified to have —OH, —$NH_2$, —COOH, SH, —$SO_3H$, —CN, and —R functional groups, thereby increasing conjugation sites on the HA polymer for the therapeutic agents.

In another general aspect there is another biologically active rapid release therapeutic agent polymer composition comprising a hyaluronic acid (HA) polymer formed of porous HA particles, the porous HA particle is formed though addition of a porogen agent having a weight ratio of between 1;10, 1:4 and 1:2 and 1;1 relative to the HA amount. There is also a therapeutic agent covalently bound to the HA polymer, and a crosslinking agent having a mole ratio of between 1:2 and 1:1 relative to the porous HA. The porous-HA particles have an average surface area between approximately 21 $m^2$/g to 0.014 $m^2$/g, an average pore volume of between approximately 11 $cm^3$/g and 1 $cm^3$/g and an average pore size of approximately 7 nm to 13 nm. The composition a rapid release therapeutic agent composition that releases a therapeutic agent to achieve a therapeutic range within approximately 24 hours and the therapeutic agent is substantially released from the HA polymer within approximately 80-120 hours after administration. The therapeutic agent can be an antibiotic, the simple carbohydrate can be sugar, the crosslinking agent can be divinyl sulfone (DVS) and the porogen can polyvinylpyrrolidone (PVP), and the antibiotic is selected from the group consisting of Ciprofloxacin and Vancomycin. The porous HA particles have an average surface area between approximately 21 $m^2$/g to 0.014 $m^2$/g, an average pore volume of between approximately 11 $cm^3$/g and 1 $cm^3$/g and an average pore size of approximately 7 nm to 13 nm, whereby surface area, pore volume, and pore size can be varied by varying crosslinker and porogen amounts relative to HA repeating units and amounts, respectively.

The composition is suspended in a chitosan solution, thereby forming a viscous suspension capable of adhering to tissue.

The composition may also further comprise binding a steroid to the HA polymer.

In still another general aspect there is a method of treating or preventing a condition using any of the compositions described above or in the detailed description. One condition may be treating a bacterial infection or preventing a bacterial infection, especially after surgery, wherein the composition achieves a therapeutically effect range within approximately 24 hours after administration and is substantially undetectable within approximately 80-120 hours of administration, thereby preventing infection and limiting the occurrence of antibiotic resistance. Treatment may be to animals or humans, and to tissues such as a liver, an eye, joint spaces, brain, and meningeal space. One specific treatment may be administering the composition to an eye, post cataracts surgery. One way to administer the composition is to administer it via a stray nozzle system.

In still another embodiment, interferons and insulin may be delivered using porous HA and modified porous HA particles, where the porous HA and modified porous HA particles can be used as carriers for delivering interferons and insulin to various parts of human body including human eyes. HA based particles can be loaded at desired amounts with interferons and insulin by placing dried HA based particles into the corresponding drug solutions in distilled water or phosphate buffer saline solution (PBS) or balanced salt solution or appropriate organic solvent. After centrifugation for separation of interferons and/or insulin loaded HA based particles, these drug loaded HA based particles can be used to prepare appropriate injectable formulations in water, PBS, or BBS. Furthermore, these drugs, such as interferons and insulin, can be chemically linked to HA based particles for the purpose of prolonged delivery into various parts of body, as these drugs have many functional groups such as —$NH_2$, —COOH and —OH and —SH.

The therapeutic agents and methods using therapeutic agents described above not only can be antibiotics, insulin, or interferons, but a wide variety of therapeutic agent types, in particular, anti-cancer agents such as Mitomycin C, 5-Fluorouacil and Cisplatin, which are capable of being bound to an HA polymer using the methods described above and in the detailed description, including linear -HA polymers and porous HA polymers with crosslinkers.

BRIEF DESCRIPTION OF THE DRAWINGS

Figure 2:
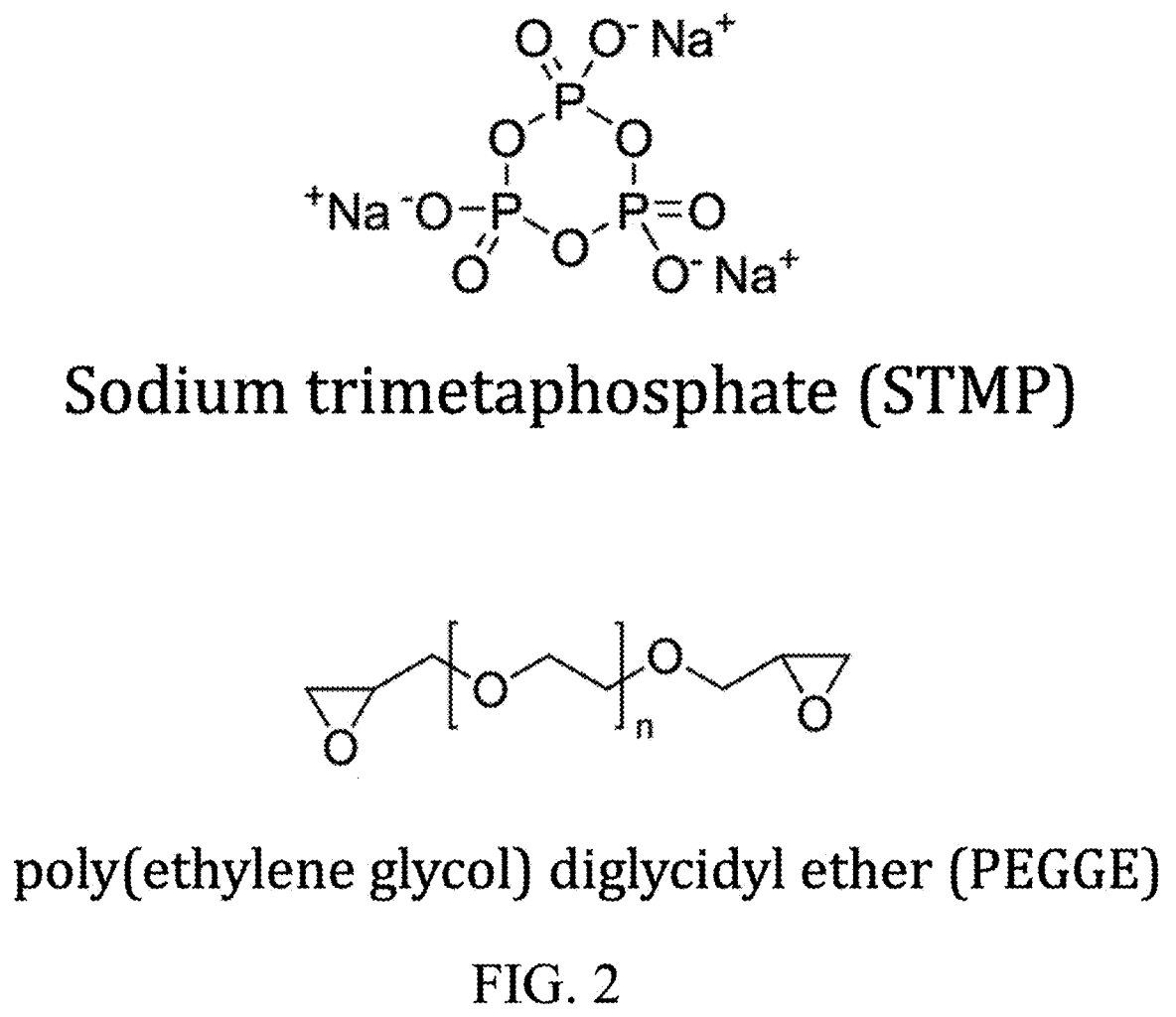

FIG. 2 depicts chemical formula of crosslinkers sodium trimetaphosphate (STMP) and poly(ethylene glycol) diglycidyl ether (PEGGE) that can be used in the preparation of HA particles;

FIG. 5*a* depicts the chemical structure of HA and antibiotic Ciprofloxacin (CP);

DETAILED DESCRIPTION OF EMBODIMENTS

Figure 1A:
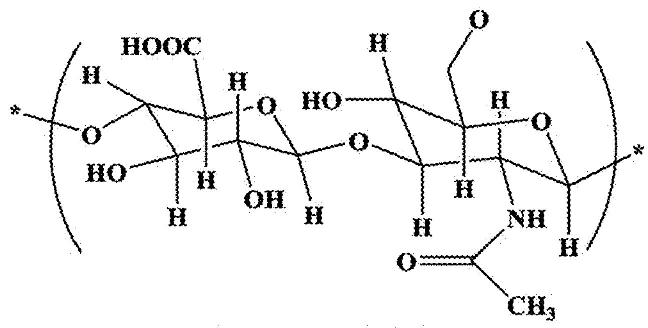
FIG. 1*a* illustrates schematic of a crosslinking reaction of linear HA to produce HA particles using GDE and TMPGDE as crosslinkers.
Figure 1A:
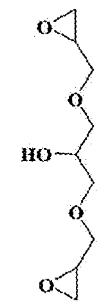
Figure 1A:
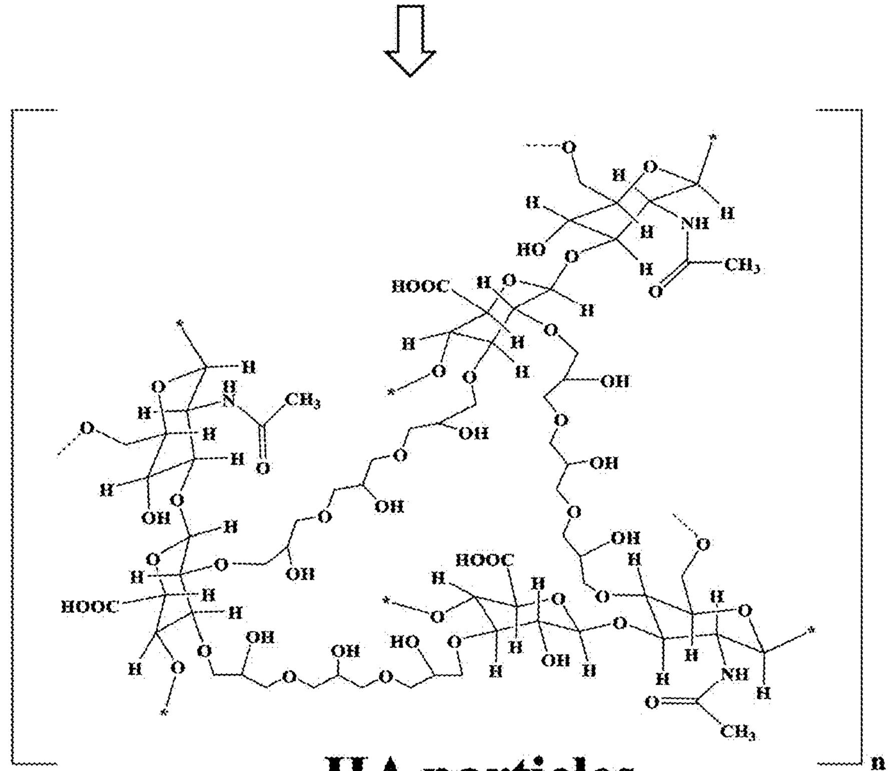
Figure 1B:
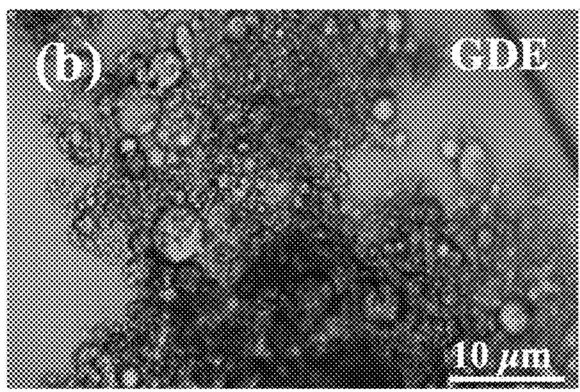
FIG. 1*b* are optical microscope images of GDE and TMP with HA, respectively.
Figure 1B:
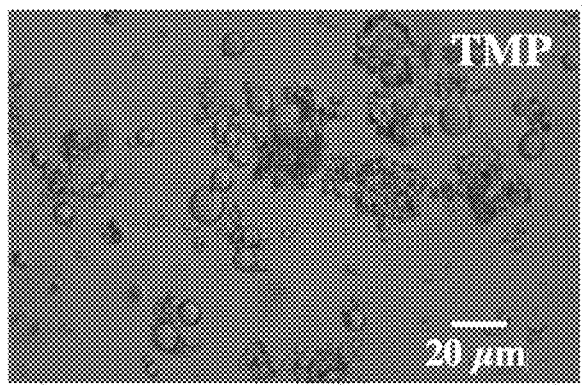
Figure 1C:
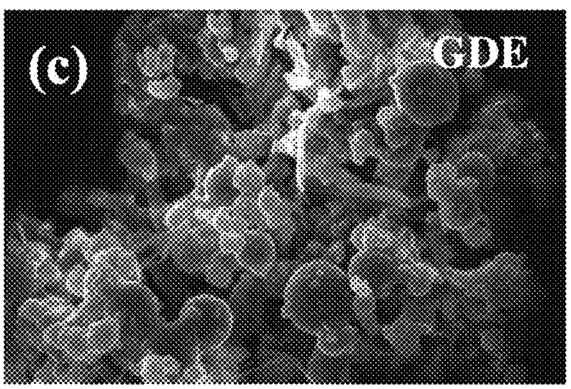
FIG. 1*c* are scanning electron microscope images of GDE and TMP with HA, respectively.
Figure 1C:

The invention now will be described more fully hereinafter with reference to the accompanying drawings, in which embodiments of the invention are shown. This invention may however be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

A "subject" or "patient" shall mean a human or animal including but not limited to a dog, cat, horse, cow, pig, sheep, goat, chicken, primate, fish, rat and mouse.

The compositions of the invention are administered in effective amounts. The term "effective amount" refers to the amount necessary or sufficient to realize a desired biologic effect. For example, an effective amount of a hyaluronic acid containing conjugate is that amount necessary to prevent or treat infection if the subject is being treated to prevent occurrence of an infection or inflammation.

As used herein, the term "treat" refers to a reduction or complete elimination of symptoms, such as but not limited to those associated infection or inflammation.

The effective amount for any particular application can vary depending on such factors as the disease or condition or location being treated, or the symptoms being alleviated, the particular conjugate being administered, the size of the subject, or the severity of the condition, or symptom. One of ordinary skill in the art can empirically determine the effective amount of a particular conjugate without necessitating undue experimentation.

As used herein, the term "simple carbohydrate" refers to monosaccharides, disaccharides, and includes, but is not limited to: sucrose, fructose, glucose, maltose, and lactose, as well as sugar alcohols.

Amounts that are described herein are idealized embodiments, but the range of acceptable amounts may be in a range of between 1% and 99%, or any subrange therein, including, but not limited to plus or minus 5%, 10%, 20%, 30%, 40%, 50%, 60%, 70%, 80%, and 90% of values disclosed.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention.

The invention provides novel compositions, methods of creation of novel compositions and treatment that would benefit from the presence of hyaluronic acid. Hyaluronic acid is known to permeabilize tissues and thus is useful for increasing the receptivity of a body tissue for another agent. The tissues so treated may be those that are under perfused either normally or due to a pathological state.

Native hyaluronic acid is a linear polymer of repeating monomers of disaccharides of D-glucuronic acid and N-acetyl D-glucosamine. As used herein, the term "hyaluronic acid" is intended to embrace native hyaluronic acid, as well as its derivatives (i.e., analogs) including but not limited to salts and esters, unless explicitly otherwise stated. Salts of hyaluronic acid include pharmaceutically acceptable salts such as sodium salts, potassium salts and ammonium quaternary salts. Hyaluronic acid derivatives include hyaluronic acid that has been modified by other chemical reactions such as esterification, and thus include hyaluronate esters, as well as sulfated hyaluronic acid (as described in U.S. Pat. No. 6,339,074 B1).

Hyaluronic acid is commercially available, and sold under a variety of brand names including Healon, Hyalastine, Hyalectin, Hyloran (sodium hyaluronate), and Hyaloftil (high molecular weight hyaluronic acid). Alternatively, hyaluronic acid can be synthesized or purified from animal sources.

Hyaluronic acid derivatives also include synthetic or semi-synthetic variants such as esters of hyaluronic acid and aliphatic, aromatic, araliphatic, heterocyclic, and cycloaliphatic alcohols (e.g., benzyl or ethyl ester of hyaluronic acid) as described in U.S. Pat. Nos. 4,851,521; 4,965,353; and 5,202,431).

As used herein, the term "conjugate" includes both direct and indirect attachment of the linking molecule to hyaluronic acid. Indirect attachment generally means that a spacer (i.e., a linker) exists between the linking molecule and the hyaluronic acid.

Conjugates may be attached to hyaluronic acid to the linking molecule by a bond that cleaves under normal physiological conditions. In still other instances, hyaluronic acid would be released in a sustained fashion, to prolong its release. Readily cleavable bonds include readily hydrolyzable bonds, for example, ester bonds, ether bonds, amide bonds and Schiff's base-type bonds.

Conjugates of hyaluronic acid with any number of linker molecules can deliver of a variety of therapeutic agents to a body tissue or surface. Hyaluronic acid is therefore intended to act as a carrier molecule for the therapeutic agent, and the hyaluronic acid itself may or may not impart therapeutic benefit. Examples of therapeutic agents that can be linked include: adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LNRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; treatment of amyotrophic lateral sclerosis; treatment of cerebral ischemia; treatment of Paget's disease; treatment of unstable angina; uricosuric; vasoconstrictor; vasodilator; vulnerary; wound healing agent; xanthine oxidase inhibitor.

As will be apparent to one of ordinary skill in the art, these latter conjugates in which hyaluronic acid is used as a carrier for other therapeutic agents can be used in therapeutic or prophylactic methods for subjects in need of such therapeutics. It is within the realm of the medical practitioner to identify subjects that would benefit from administration of such agents.

Experiment 1: Controlled Rapid Release Drug Delivery System for Peri and Immediate Postoperative Infection Prophylaxis An HA based antibiotic delivery system releases therapeutic levels of antibiotics in the peri and immediate postoperative period.

Antimicrobial activity and biocompatibility of Hyaluronic acid-conjugate polymer provides sufficient sustained release of antibiotic after ophthalmic surgery with equal efficacy as topical antibiotic therapy on pathogenic bacteria and does not cause significant toxicity to eukaryotic cells.

The following procedure was used to determine the efficacy and toxicity of an HA based antibiotic delivery system after ophthalmic surgery by evaluating the drug release rate of the HA-antibiotic polymer over time, the antimicrobial activity of the HA-antibiotic polymer over time, the biocompatibility of HA-antibiotic polymer in vitro on fibroblasts, and the corneal toxicity of the HA-antibiotic polymer.

Methods

Hyaluronic acid sodium salt from *Streptococcus equi* was purchased from Sigma Aldrich. Glycerol diglycidyl ether (GDE) (technical grade, Aldrich) as crosslinker, sodium bis(2-ethylhexyl) sulfosuccinate (AOT, 98%, Sigma-Aldrich) as a surfactant, and 2,2,4-trimethylpentane (isooctane) (ACS, Reag. Ph Eur, 99.5%) as a solvent, were used as received. 1,1'-carbonyldiimidazole (≥97%, Sigma-Aldrich) was as coupling agent. All the solvents, acetone (puriss., 99%, Sigma-Aldrich) and dimethyl sulfoxide (puriss., ACS reagent, 99.5%, Sigma-Aldrich) were of the highest purity available. Ultrapure distilled water 18.2 MΩ cm (Millipore-Direct Q UV3) was used throughout the studies. Ciprofloxacin (≥98%, HPLC grade, Sigma-Aldrich) and Vancomycin obtained from a local vender (≥98.0%, Mustafa Nevzat Pharmaceuticals, Turkey).

Synthesis of HA Particles

HA particles were synthesized as follows. Linear HA was dissolved in 0.2 M NaOH at a concentration of 50 mg/L. Then 1.08 mL of this HA solution was dispersed in 30 mL of 0.2 M AOT solution in isooctane. The mixture was immediately vortexed until a clear suspension was obtained. A certain amount of GDE (e.g., 50 mole percent relative to the HA repeating unit) was subsequently added to the mixture, which was then vortexed again to disperse the GDE. The reaction was allowed to proceed for 1 h at ambient temperature with vigorous stirring (1200 rpm). Then, the obtained particles were precipitated in excess of acetone and purified by centrifugation at 10,000 rpm for 10 min at 20° C. This was followed by removal of the supernatant solution and re-dispersal with acetone and re-centrifugation at least three times. The prepared particles were dried with a heat gun and kept in a closed container for further use.

Synthesis of HA:Sucrose Copolymeric Particles

HA:Sucrose (HA:Suc) copolymeric particles with DVS crosslinker were synthesized in a single step. Briefly, linear HA was dissolved in 0.2 M NaOH at a concentration of 50 mg/mL. Separately, 82 mg/mL concentration of sucrose solution was prepared the same mole ratio of HA repeating unit. Then, 1 mL of the HA solution and 0.5 mL of the sucrose solution was mixed, and 1 mL of this mixture was dispersed in 30 mL of 0.2 M AOT solution in isooctane. The mixture was immediately vortexed until a clear suspension was obtained. DVS (125 mole percent relative to the mixture materials repeating unit) as crosslinker was subsequently added to the mixture, which was then vortexed again to disperse the crosslinker. The reaction was allowed to proceed for 1 h at ambient temperature with vigorous stirring (1,000 rpm). Then, the obtained particles were precipitated in excess of acetone and purified by centrifugation at 10,000 rpm for 10 min at 20° C. This was followed by removal of the supernatant solution and re-dispersal with acetone and re-centrifugation at least three times. The prepared particles were dried with a heat gun and kept in a closed container for further use.

Synthesis of Ciprofloxacin/Vancomycin Conjugates Particles

Synthesis of Ciprofloxacin conjugated particles

HA and HA:Suc particles were conjugated with Ciprofloxacin. Shortly, 0.532 g of Ciprofloxacin were dissolved in 10 mL DMSO solution. Then, 0.286 g of 1,1'-carbonyldiimidazole was added to this solution and stirred at room temperature for 1 h. Subsequently, 0.84 g HA particles was added to the drug mixture and the reaction was allowed to react for 24 h at 80° C. under stirring. The conjugated HA particles was washed with DMSO one time and washed with acetone two times and dried with freeze dryer.

Synthesis of Vancomycin Conjugated Particles

HA and HA:Suc particles were conjugated with Vancomycin. Shortly, 0.42 g of Vancomycin were dissolved in 10 mL DMSO solution. Then, 0.286 g of 1,1' carbonyldiimidazole was added to this solution and stirred at room temperature for 1 h. Subsequently, 0.84 g HA particles was added to the drug mixture and the reaction was allowed to react for 24 h at 80° C. under stirring. The particles were washed with DMSO one time and washed with acetone two times and dried with freeze dryer.

Drug Release Experiments

30 μg of HA-antibiotic particles was placed into 1.5 mL Eppendorf tubes and 250-500 μL of Balanced Saline Solution (BSS) was added to the Eppendorf tubes and the mixture was vortex until well mixed. The drug mixture was then placed in a shaker at 37° C. and allowed to incubate.

At each time point e.g., 1 hour, 2 hour, 3 hour, 6 hour, 24 hour, 48 hour, 72 hour, 96 hour, 1 week, 2 week, 3 week and 4 week-, 50 μL of the mixture was removed and an equivalent volume of new BSS added back to the tubes. This was repeated each time a sample was removed for determination of drug release.

Measuring Released Amount of Drug

A standard curve was established using known concentrations of Ciprofloxacin and Vancomycin, and the absorbance values were measured at 275 and 280 nm, respectively, using the NanoDrop UV-Vis Spectrophotometer This was then plotted using Excel and a standard curve with equation established.

With each drug release collection, the Drop UV-Vis Spectrophotometer was used to measure the light absorbance, and the drug concentration then calculated using the previously established standard curve.

Antimicrobial Experiments

Antimicrobial activity of the released drug was tested on *Pseudomonas aeruginosa* and MRSA cultures and compared to standard concentrations of antibiotic using filter disks on Mueller Hinton plates. The released antibiotics or controls were added onto sterile filter discs (created using a standard hole punch on filter paper, autoclaved). One colony of each bacteria was selected and (pseudomonas or MRSA) placed into a bacteria culture tube and were incubated in 5 mL of LB broth and placed on 37° C. shaker for approximately 4-6 hours.

500 μL of the incubated bacteria was then added to the Mueller-Hinton Plates (which have been acclimated to room temperature for at least 2 hours) and a plastic disposable spreader was used to carefully spread the bacteria broth onto the plates and allowed to settle for approximately 5-10 minutes. The filter discs were then placed on top of the bacterial plate and the plates inverted and placed in the 37° C. incubator overnight. After 24 hours, the plates were removed and the zones of inhibition measured and photographed. Parafilm was used to wrap around each plate to keep the plates at room temperature.

Cytotoxicity Experiments $10^5$ smooth muscle cells were plated into each well of 12-well plates and allowed to settle for 1 hour in 2.5 mL of complete culture media (DMEM+10% FBS+antibiotics+amino acids). The cells were allowed to grow to 70-80% confluence. Meanwhile, various concentrations of HA-antibiotic conjugate, HA particles, and antibiotics were suspended in complete media and added to the wells. The cells were incubated at 37° C., 95% $CO_2$ for 5 days. Following the incubation period, DMEM was removed cells were fixed in glutaraldehyde then stained with toluidine blue and resuspended in SDS. A cell counter was then used to quantify the absorbance of the stain to quantify and compare the number of cells in each group. The plates were photographed, then resuspended and then a UV spectrophotometer used to measure the light absorbance of the cell density.

Corneal Thickness

Human donor corneas were obtained from the Southern eye bank and suspected in optisol solution. The pachymetry was measured using a standard corneal pachymeter. 30 and 90 μg of HA-antibiotic was then added to the cornea in optisol and allowed to incubate for 5 days. After 5 days, the corneal pachymetry was again measure and the endothelial cells were observed under high magnification light microscopy.

RESULTS

Rate of Drug Release of the Hyaluronic Acid-Ciprofloxacin and Hyaluronic Acid-Vancomycin Conjugate Polymer The released amount of antibiotics (Ciprofloxacin and Vancomycin) from the conjugated HA-Ciprofloxacin particle was quantified using NanoDrop UV-Vis Spectrophotometer.

There was an immediate release of 130 mg of Ciprofloxacin per g of polymer every hour in the first 2 hours, followed by a fast release of 670 mg per g in the first 24 hours. The total released was 820 mg over 7 days. There was a linear trend of release. Similarly, there was an immediate release of 50-80 mg/g of Vancomycin in the first 2 hours, and a fast release of 230 mg per g of polymer in the first 24 hours. A similar linear rate of release is seen at 6 hours.

Antimicrobial Activity

Antimicrobial activity of the released drug was tested on *Pseudomonas aeruginosa* and MRSA cultures and compared to standard concentrations of Ciprofloxacin and Vancomycin, respectively, using filter disks on Mueller Hinton plates. The control studies show that only 5 μg of Ciprofloxacin, and 10 μg of Vancomycin is sufficient to inhibit pseudomonas and MRSA growth, respectively, and provide a zone of inhibition that is well above the MIC.

The released Ciprofloxacin and Vancomycin were able to provide sufficient inhibition of pseudomonas and MRSA growth, respectively at every time point of collection between 1 hour and 7 days (zone of inhibition up to 15 mm). After 1 weeks, the rate of drug release appeared to be too low for inhibition of bacterial growth.

The control studies show that only 10 μg of Vancomycin on a filter disc was sufficient to inhibit MRSA growth and provide a zone of inhibition of 8 mm. Published studies show that the minimum inhibitory concentration of Ciprofloxacin is 0.5 mg/L and Vancomycin is 2 mg/L. In 250 μL, the volume of the human anterior chamber, the amount of antibiotic released using the polymer was far in excess of the MIC. In addition, to simulate the constant outflow of aqueous humor and thus gradual decline in drug concentration in the eye, we removed 25% of the supernatant in the drug release collections each time we collected the sample and replaced with BSS, thus removing a significant amount of the drug each time, allowing antimicrobial testing using the actual change in drug concentration and not a cumulative effect. 20 mg of HA-Ciprofloxacin and 30 mg of HA-Vancomycin were sufficient and effective at preventing bacterial growth at every time point between 1 hour and 7 days, with zones of inhibition up to 15 mm and 12 mm, respectively Cytotoxicity Studies The HA-antibiotic polymers showed no effect on fibroblast cell proliferation over 5 days under normal culture conditions. The presence of HA polymers did not change the cell division or proliferation rates compared to control, where cells were cultured in the absence of any additional polymers.

Corneal Thickness Studies

Figure 4:
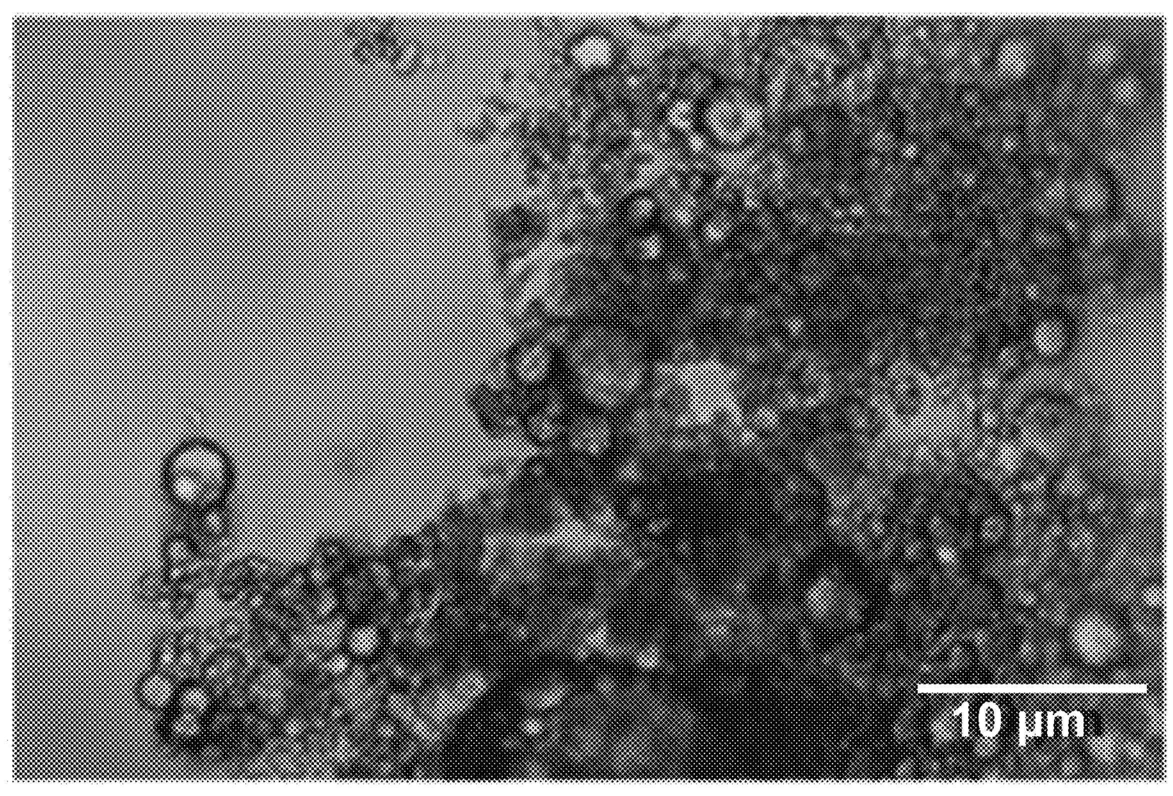
FIG. 4 depicts optical microscope images of HA particles crosslinked with GDE.
Figure 4:
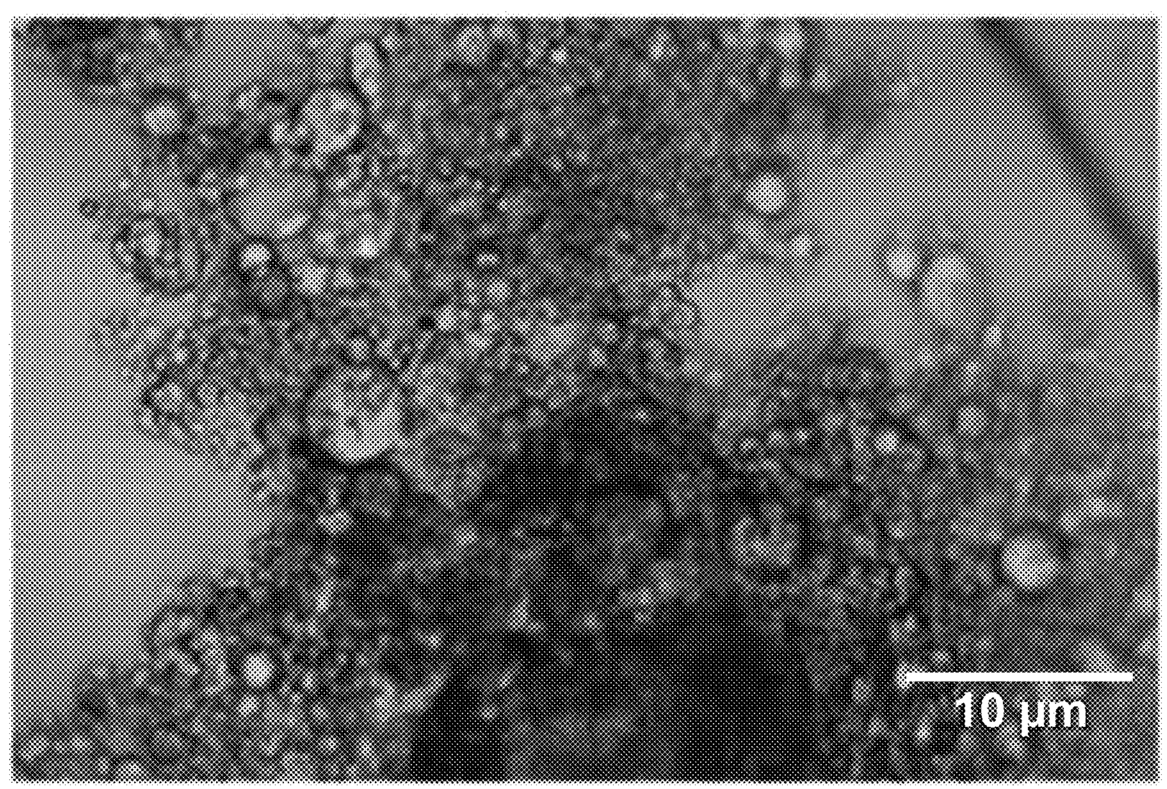

The presence of HA-antibiotic polymers had no effect on corneal thickness over 5-day incubation period. FIG. 4 shows the optical microscopy imaged of HA particles crosslinked with GDE.

Figure 5A:
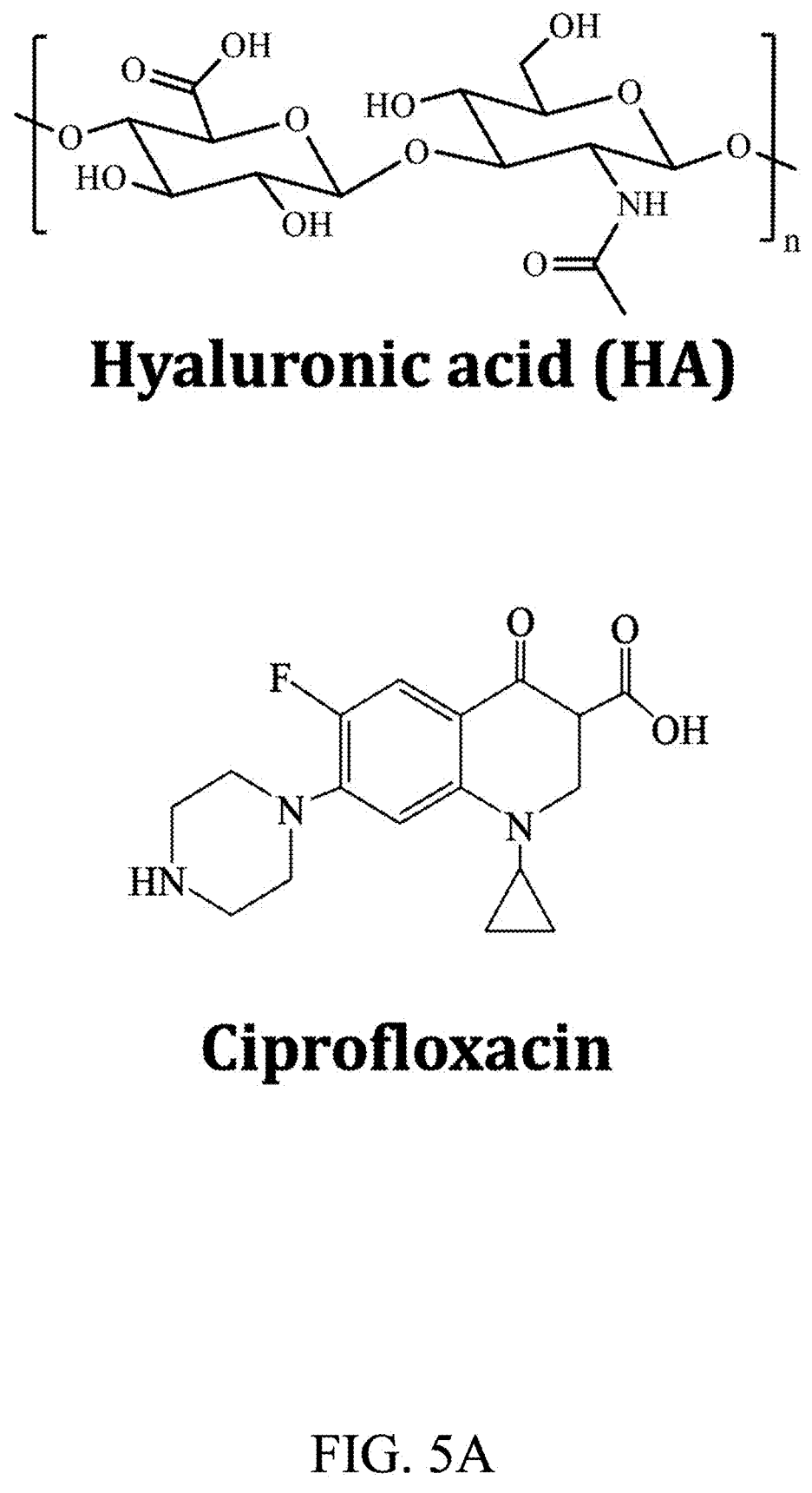
Figure 5B:
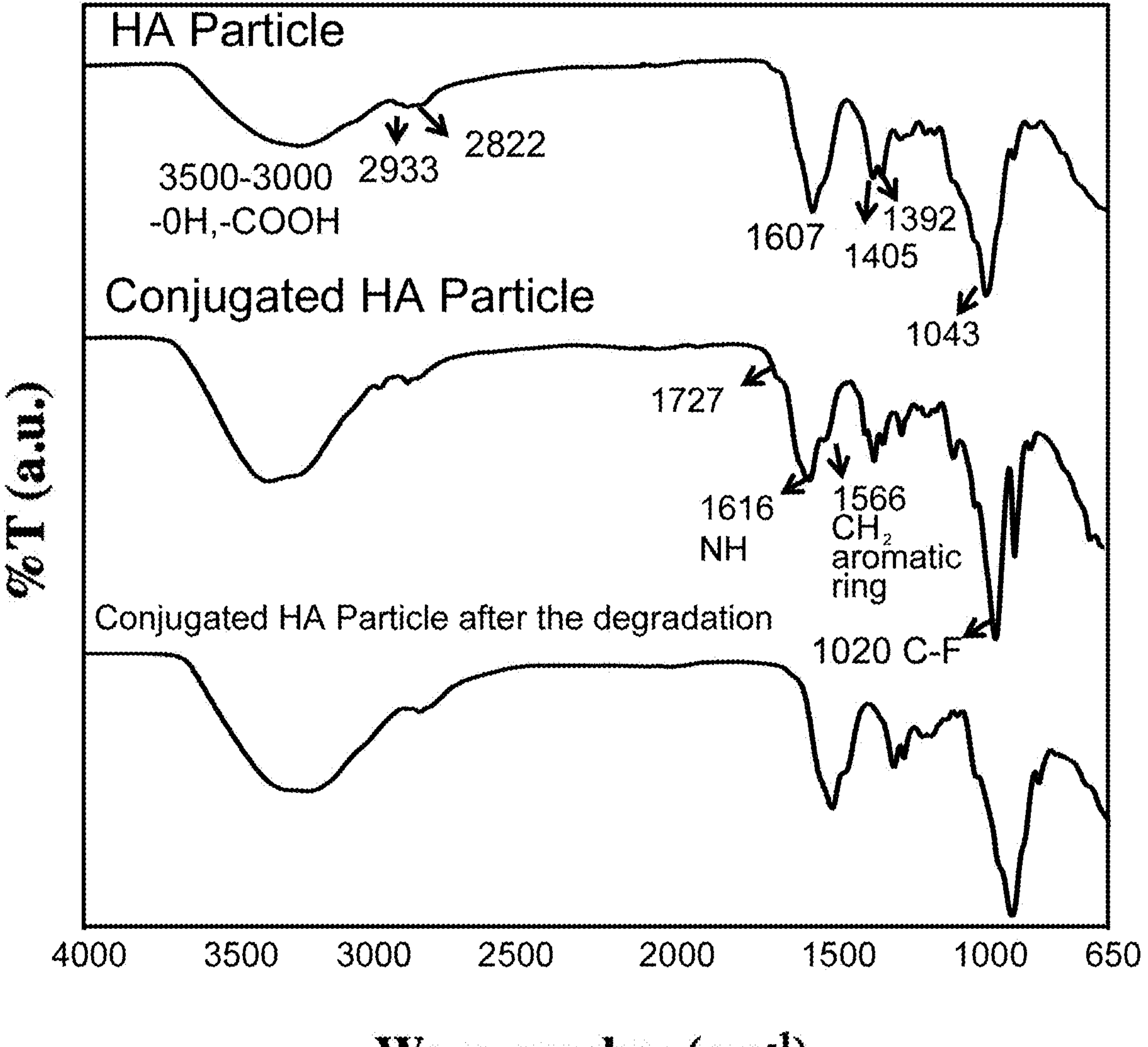
FIG. 5*b* is a graphical representation of FT-IR spectra of bare HA particles, Ciprofloxacin conjugated HA particles (CP-HA), and CP-HA particles after CP release in PBS at 37.5° C.

To confirm the conjugation of Ciprofloxacin (CP) to HA particles (CP-HA), FT-IR spectra of bare HA and CP-HA was recorded using FT-IR spectroscopy (Perkin Elmer Spectrum 100). The chemical structure of HA and CP and the specific peaks for bare HA were given as (a) and (b), respectively in FIG. 5. Specifically, FIG. 5*a* depicts the chemical structure of HA and CP, and FIG. 5*b* depicts FT-IR Spectra of bare HA particles, CP conjugated HA particles (CP-HA), and CP-HA particle after CP release in PBS at 37.5° C.

Figure 6:
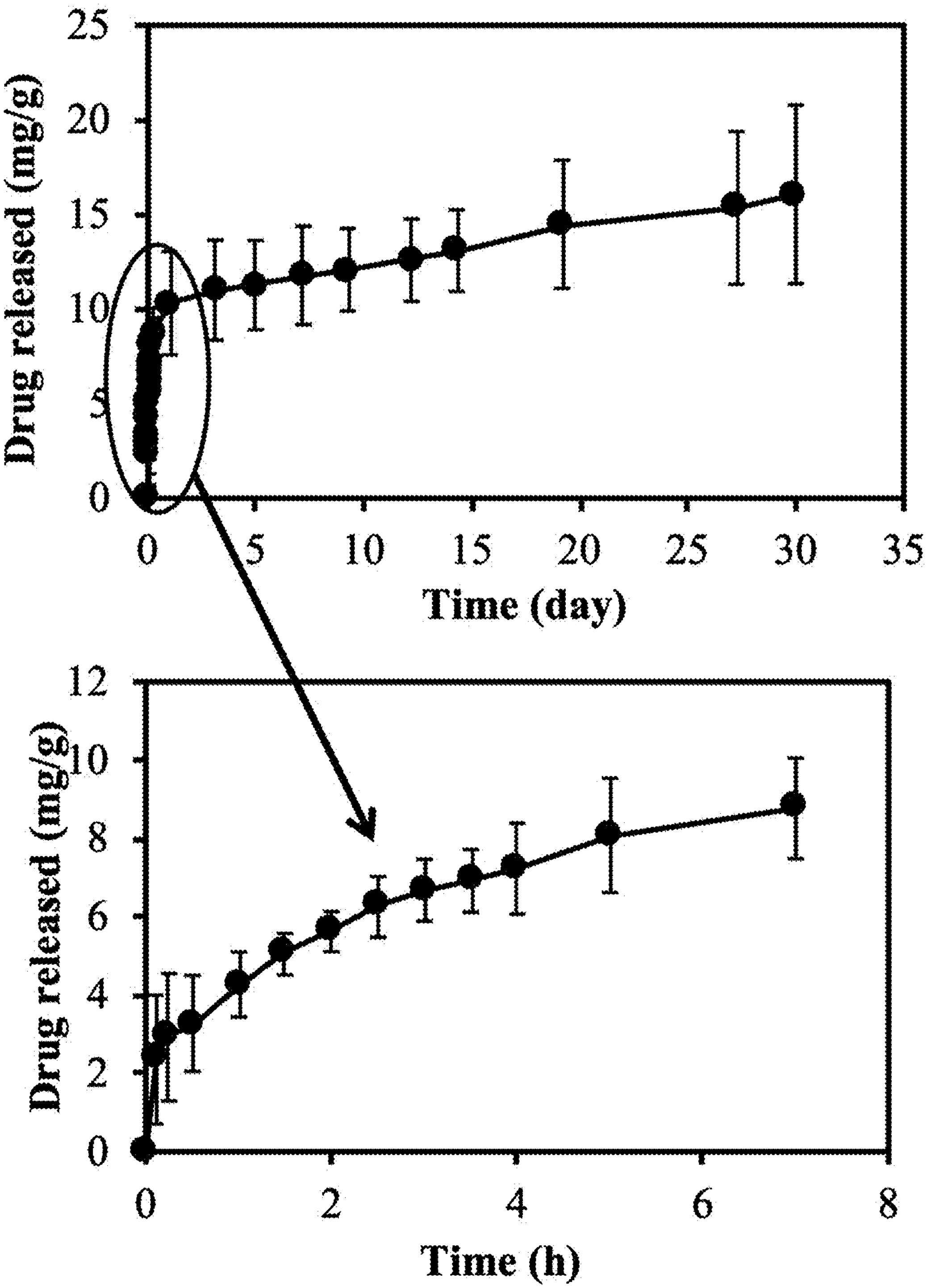
FIG. 6 is a graphical representation of Ciprofloxacin (CP) release profile from CP-HA particles in phosphate buffer saline at (PBS) at 37.5° C.

The released amount of drug from CP-HA conjugates were determined by UV-Vis spectrometer and the constructed graph is depicted in FIG. 6, which shows the CP release profile from CP-HA particle in phosphate buffer saline (PBS) at 37.5° C.

For the Vancomycin assay, a similar procedure was used to assess the Vancomycin HA combination, except the test bacteria was *Staphylococcus aureus* and similar results as above were produced (not shown).

CONCLUSION

The above experiment shows that surgical outcome and patient quality of life would be greatly improved by a fast drug releasing system that could be administered at time of ocular surgery and decrease risk of post-operative infections while also eliminating or minimizing the need for topical medications.

Experiment 2: HA: Sucrose Copolymeric Particles

Antimicrobial Studies

Four different bacteria; gram-positive *Staphylococcus aureus* ATCC 6538 and *Bacillus subtilis* ATCC 6633 and gram-negative *Escherichia coli* ATCC 8739 and *Pseudomonas* aeroginosa ATCC were cultured in different growing media separately. Certain amounts (40, 20, 10, 5, 2.5 mg) of HA particles, HA:Sucrose particles, Conjugated HA particles and HA:Sucrose particles with Ciprofloxacin and Vancomycin were put into 10 mL of nutrient broth and sterilized by irradiation with UV light at 420 nm for 2 min. Then, 0.1 mL of bacteria culture adjusted against McFarland 0.5 standard nearly $1\times10^8$ CFU/mL were added to the growing media and incubated at 35° C. for 18-24 h. After then, 0.1 mL from the cultures in each medium were tube was placed on agar plate for enumeration of colonies. Minimum inhibition concentration (MIC) values was determined as the minimum concentration of antimicrobial material where no turbidity (visible growth) in NB medium. Minimum bactericidal concentration (MBC) values were determined as the lowest concentration of antimicrobial materials that can inhibit 99.9% of microorganisms.

Figure 7A:
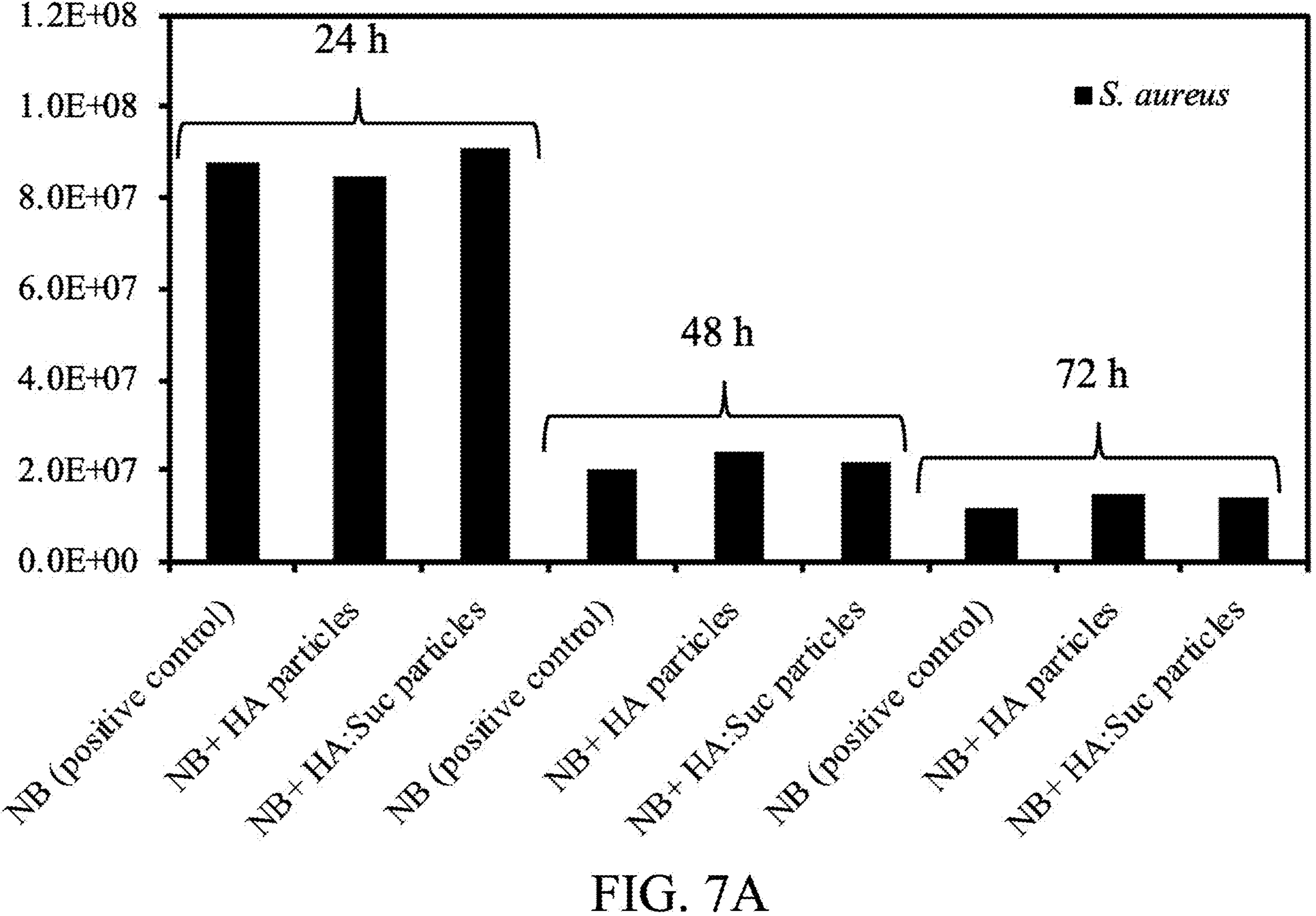
FIG. 7*a* is a graphical representations of numbers of bacterial (colony forming unit/mL *S. aures*) growing in different media such as Nutrient Broth (NB, positive control), HA and HA:sucrose particles in the presence NB at 24 h, 48 h, and 72 h incubation times.
Figure 7B:
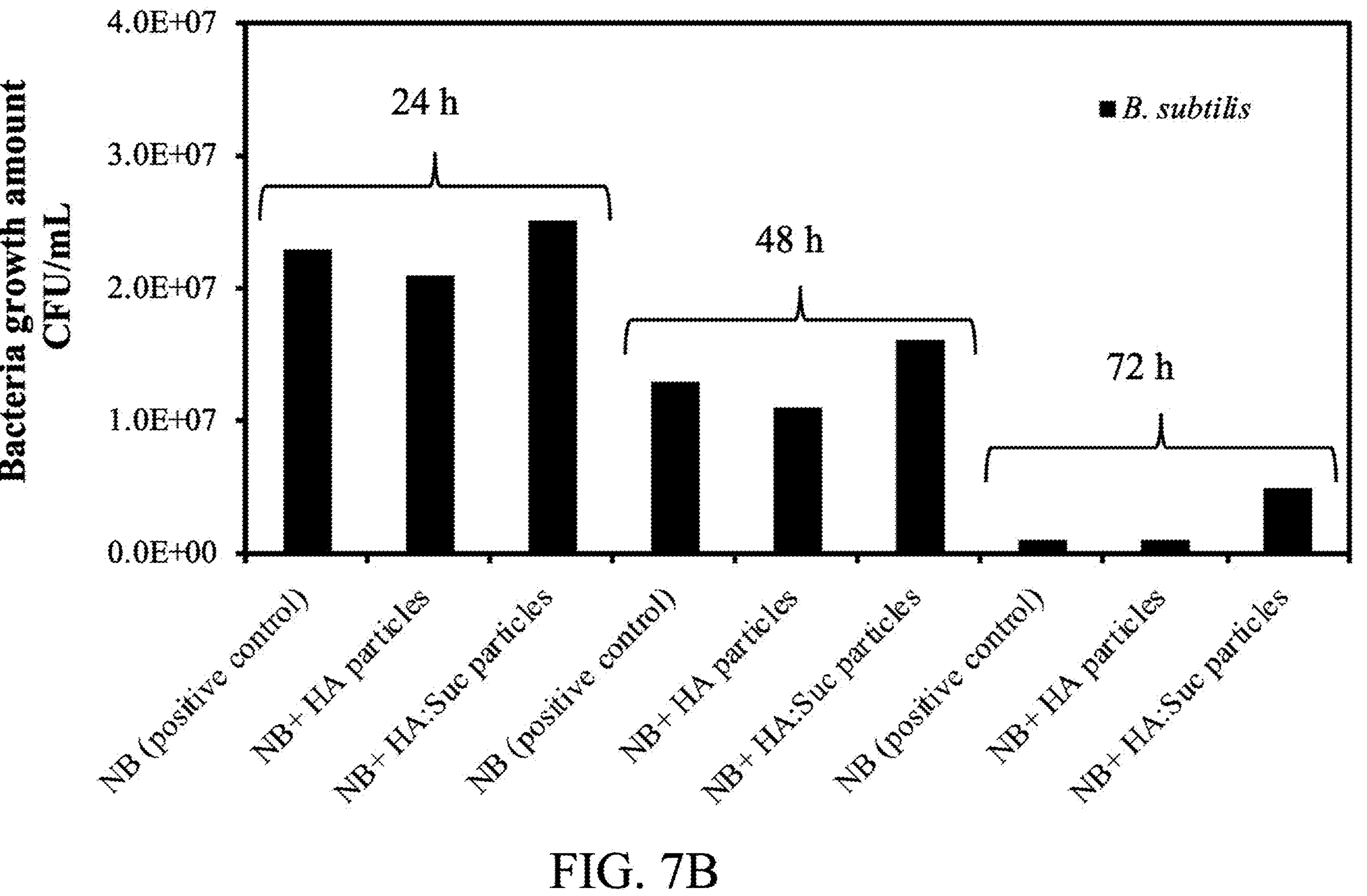
FIG. 7*b* is a graphical representations of numbers of bacterial (colony forming unit/mL *B. subtilis*) growing in different media such as Nutrient Broth (NB, positive control), HA and HA:sucrose particles in the presence NB at 24 h, 48 h, and 72 h incubation times.

As shown in FIG. 7, the presence of sucrose in HA-sucrose particles promotes or enhances B. *Subtilis* growth at 24, 48 72 h incubation time and enhances or do not affect S. *Aureus* growth.

As shown in Table 1, for HA and HA-sucrose particles there are no MIC and MBC values for 24 h incubation time.

TABLE 1

Minimum inhibition concentration (MIC) and minimum bactericidal concentration (MBC) values of HA particles and HA:Suc particles against *Bacillus subtilis*, *Staphylococcus aureus*, *Escherichia coli*, and *Pseudomonas aeruginosa*.

| | MIC (mg/mL) | | | MBC (mg/mL) | | |
|---|---|---|---|---|---|---|
| Bacteria | 1. | 2. | 3. | 1. | 2. | 3. |
| | HA particles | | | | | |
| *B. subtilis* (Gram +) | — | — | — | — | — | — |
| *S. aureus* (Gram +) | — | — | — | — | — | — |
| *E. coli* (Gram −) | — | — | — | — | — | — |
| *P. aeruginosa* (Gram −) | — | — | — | — | — | — |
| | HA:Suc particles | | | | | |
| *B. subtilis* (Gram +) | — | — | — | — | — | — |
| *S. aureus* (Gram +) | — | — | — | — | — | — |
| *E. coli* (Gram −) | — | — | — | — | — | — |
| *P. aeruginosa* (Gram −) | — | — | — | — | — | — |

Upon testing the bacteria with Ciprofloxacin conjugated HA particles (HA-CP) and Ciprofloxacin conjugated HA-Sucrose particles there are MIC and MBC values at certain concentration of the particles as summarized in Table 2.

TABLE 2

Minimum inhibition concentration (MIC) and minimum bactericidal concentration (MBC) values of Ciprofloxacin conjugated HA particles and Ciprofloxacin conjugated HA:Suc particles against *Bacillus subtilis*, *Staphylococcus aureus*, *Escherichia coli*, and *Pseudomonas aeruginosa*.

| | MIC (mg/mL) | | | MBC (mg/mL) | | |
|---|---|---|---|---|---|---|
| Bacteria | 1. | 2. | 3. | 1. | 2. | 3. |
| | Ciprofloxacin conjugated HA particles | | | | | |
| *B. subtilis* (Gram +) | 0.25 | 0.25 | 0.25 | — | 1 | 0.5 |
| *S. aureus* (Gram +) | 2 | 2 | 2 | 4 | 2 | 2 |
| *E. coli* (Gram −) | >0.5 | >0.5 | >0.5 | 1 | 1 | 1 |
| *P. aeruginosa* (Gram −) | 0.25 | 0.25 | 0.25 | 0.5 | 0.5 | 0.5 |
| | Ciprofloxacin conjugated HA:Suc particles | | | | | |
| *B. subtilis* (Gram +) | 2 | 0.5 | 0.4 | 4 | 4 | 4 |
| *S. aureus* (Gram +) | 1 | 0.5 | 0.5 | 2 | 2 | 1 |
| *E. coli* (Gram −) | 0.5 | <0.25 | <0.25 | 1 | 0.25 | 0.25 |
| *P. aeruginosa* (Gram −) | 0.25 | 0.25 | 0.25 | — | 0.5 | 0.25 |

Experiment 3: HA-Antibiotic System Suspended in Chitosan for Surface Application One use for an HA-antibiotic delivery system suspending in chitosan is the ability of this system to adhere or form a viscous layer on tissue such as an eye. This system would be especially useful during cataract surgeries, where infections pose a significant problem. Current use of antibiotics on the eye require the use of antibiotic drops before, during, and after surgery. However, by using an HA-antibiotic chitosan suspension, the medical provider could add a drop of the solution and have a therapeutically effective amount of antibiotic release within approximately 4-6 hours, and have the antibiotic levels drop to below detectable levels (thereby preventing antibiotic resistance). Similar application of a HA-antibiotic chitosan suspension could be effective for joint spaces and other tissues.

Methods

Figure 3:
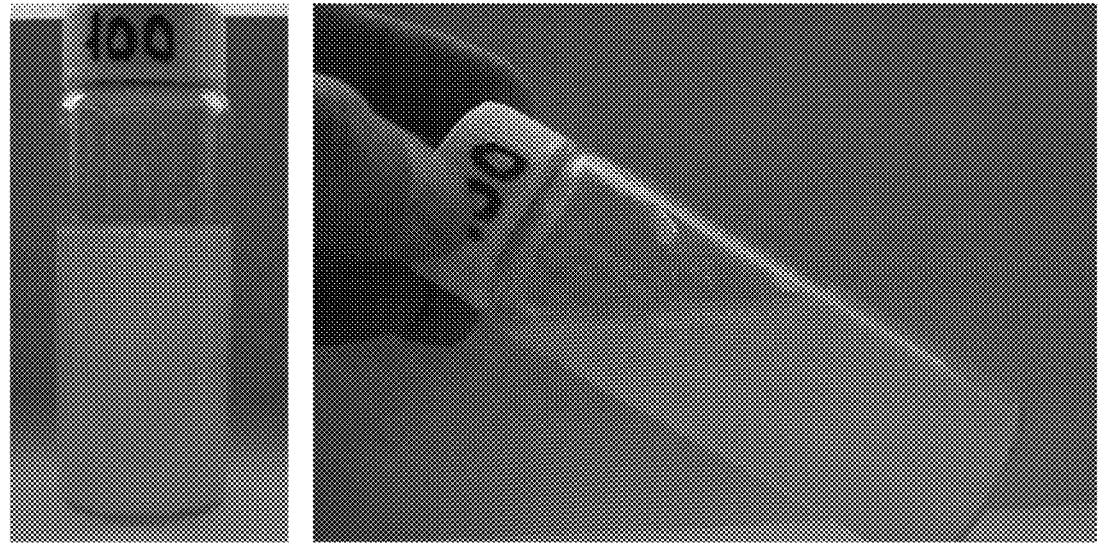
FIG. 3 depicts photographs of HA particles suspended in a chitosan solution.

Chitosan solution was prepared for HA suspension and preloaded into a spray nozzle system. 0.5 g chitosan was dissolved in 25 mL of 1% acetic acid solution in DI water and 100 mg conjugated HA-Ciprofloxacin particles are suspended into this chitosan solution. Then, chitosan coated HA-Ciprofloxacin particles were centrifuged at 10,000 rpm to separate from acetic acid solution. Finally, chitosan coated HA-Ciprofloxacin were resuspended in PBS or BBS at desired concentration. A photograph of the suspension of the HA-Ciprofloxacin conjugate with chitosan is shown in FIG. 3.

HA-Antibiotic conjugates (Vancomycin or Ciprofloxacin) should be added to the chitosan nozzle system and delivered to anterior segment portion of eye bank eyes (specifically, the cornea and conjunctival surface). These treated eye balls should be suspended in BSS Plus to mimic tears (1.5cc) in a small sterile dish to mimic the tear film system. The BSS solution should replaced every day and assessed for the antibiotic concentration using HPLC analysis. This procedure should be repeated for 5 days followed by specular microscopy of the corneal endothelium (to study potential effects on corneal endothelium).

Experiment 4: Porous HA Particles

Materials and Methods

Materials

Sodium hyaluronate (HA-EP3, Bloomage Freda Biopharm Co. Ltd.) was used as received. Polyvinylpyrrolidone (PVP, average mol wt 40,000, Sigma Aldrich) as a porogen agent, divinyl sulfone (DVS) (98%, Merck), as crosslinker, sodium bis(2-ethylhexyl) sulfosuccinate (AOT, 98%, Sigma-Aldrich) as a surfactant, trimethylolpropane triglycidyl ether (TMPGDE) (technical grade, Aldrich) as a modifying agent were used as received. as solvent were used as received. All the solvents, 2,2,4-trimethylpentane (isooctane) (99.5%, Carlo Erba), isopropyl alcohol (IPA, puriss., meets analytical specification of Ph. Eur. ≥99.5 GC, Sigma Aldrich), acetone (99%, BRK), and ethanol (99%, Birkim) were used of the highest purity available. Ultra-pure distilled water 18.2 MΩ cm (Millipore-Direct Q UV3) was used throughout the studies.

Synthesis of HA Particles with Different Amounts Cross-linking Ratio

HA microparticles with different crosslinker degree of were synthesized according to the procedures reported previously with some modifications. Briefly, linear HA was dissolved in 0.2 M NaOH at a concentration of 30 mg/mL. Then, 1 mL of this HA solution was dispersed in 30 mL of 0.2 M AOT solution in isooctane. The mixture was immediately vortexed until a clear suspension was obtained. After 1 hour, different ratio of DVS as a crosslinker at 1, 2.5, 5, 10, 25, 50, 100 mol % relative to the HA repeating unit were added to the mixture, which was then vortexed again to disperse the crosslinker, separately. The reaction was allowed to proceed for 1 hour at ambient temperature with vigorous stirring (1,000 rpm). Then, the obtained particles were precipitated in excess of acetone and purified by centrifugation at 10,000 rpm for 10 min at 20° C. This was followed by removal of the supernatant solution and redispersal with acetone and water mixture and centrifugation at least five times. The prepared particles were swollen in DI water, dried with a freeze-dry and kept in a closed container for further use.

Characterization of HA Particles

Size and morphological characterization of the HA particles were visualized by using optic microscope (Olympus BX51) and scanning electron microscope (SEM Jeol JSM-5600 LV) instrument operating at 20 kV voltage. The certain amount of HA particles was placed on a carbon tape attached SEM stub and coated with a few nm thicknesses of gold under vacuum.

The dynamic light scattering (DLS) experiments were carried out at 900 angle detector using Brookhaven Ins. and Cor. 90 plus particle size analyzer, with 35 mW solid state laser detector operating at a wavelength of 658 nm. The results were the average values of consecutively ten measurements with an integration time of 2 seconds. Zeta potential measurements were conducted with Zeta-Pals Zeta Potential Analyzer BIC (Brookhaven Inst. Corp.) in 0.01 M KCl solution in water. Each measurement was repeated at least three times.

The functional groups of the HA particles were determined by using a Fourier Transform Infrared Radiation Spectroscopy (FT-IR, Perkin-Elmer) in the spectral range 4000-650 $cm^{-1}$ at 4 $cm^{-1}$ resolution using attenuated total reflectance (ATR). Thermal degradation of HA and HA particles were carried out using thermogravimetric analyzer (SII TG/DTA 6300, Japan). Nearly 5 mg of the materials was heated with 10° C./mL heating rate up to 1000° C. under inert atmosphere using $N_2$ gas with 100 mL/min flow rate.

The specific surface areas, the pore volume and average pore width of the HA particles were performed by a Tristar II Surface Area and Porosity Analyzer using the Brunauer-Emmett-Teller (BET) and Barret-Joyner-Halenda (BJH) methods, respectively. For removed contaminants and wetness, HA particles were degassed by using a FlowPrep 060 Degasser at 100° C. for 5 h prior to adsorption analysis.

Results

Lower Amounts of DVS (<20 Mole % of HA Repeating Unit) for Porous HA Particles

Hyaluronic Acid particles are synthesized according to the literature using divinyl sulfone as crosslinker DVS in sodium bis(2-ethylhexyl) sulfosuccinate (AOT) isooctane microemulsion systems. In the literature, a minimum of 20 mole % DVS based on HA repeating unit is reported, and above this concentration of DVS usage result in nonporous HA microparticles.

Figure 8:
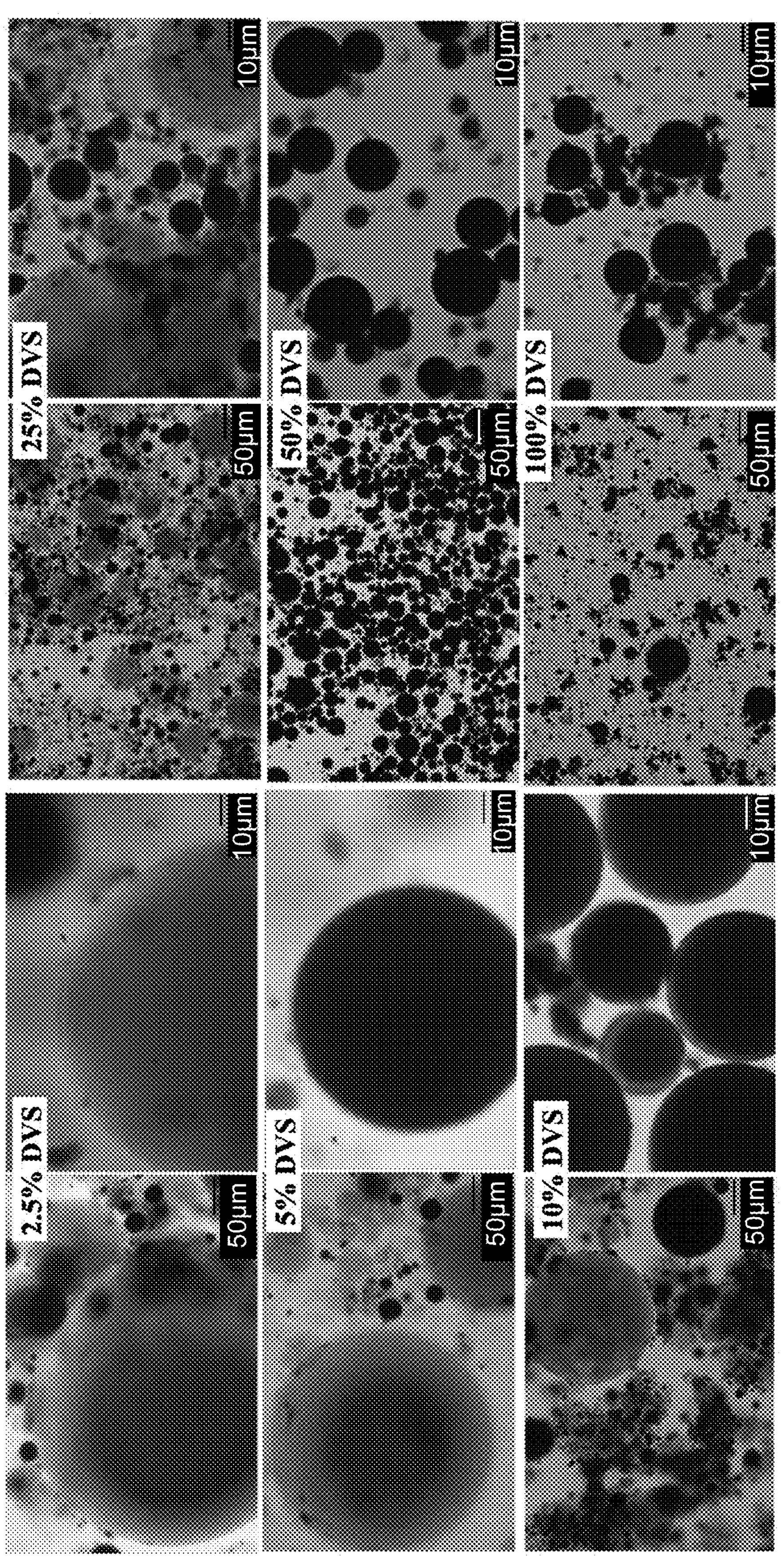
FIG. 8 depicts optical microscope images of HA microparticles crosslinked with DVS at different mole ratio (2.5, 5, 10, 25, 50, and 100% mole ratio relative to the HA repeating unit)

Here, we report the use of DVS less then (<20 mole %) of based on HA repeating units that enable porous HA particles. Optical microscopy images as shown in FIG. 8, reveal that HA particles can be even prepared by using 2.5% DVS. It is clear that the HA particles prepared are spherical and the size ranges changes between few hundred nm to few hundred micrometers. Specifically, FIG. 8 depicts optical microscope images of HA microparticles crosslinked with DVS at different crosslinking mole ratios (2.5, 5, 10, 25, 50, 100% mole ratio based on the HA repeating unit).

Figure 9:
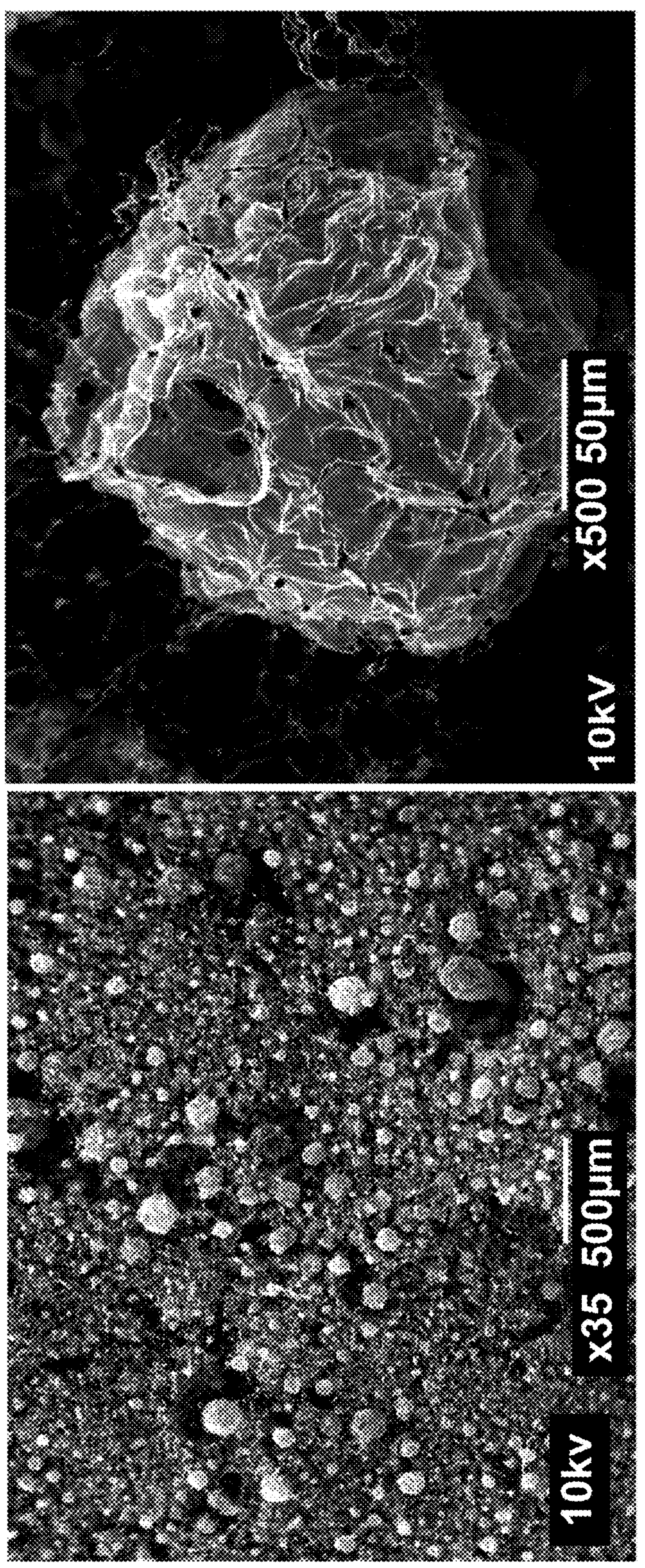
FIG. 9 depicts scanning electron microscope images of HA microparticles crosslinked with 5% DVS at different magnifications in 0.2M AOT-isooctane solution.

The SEM images further illustrates the porous structure of HA particles as shown in FIG. 9, and revealed that HA particles using 5% DVS are porous. Specifically, FIG. 9 depicts scanning electronic microscope images of HA microparticles crosslinked with 5% DVS at different magnifications in 0.2 M AOT-isooctane solution.

Table 3 summarizes the Brunauer-Emmett-Teller (BET) (Micromeritics TriStar II) analysis result of HA particles prepared at different crosslinking ratio of DVS based on the HA repeating unit.

TABLE 3

Surface area, pore volume, and pore size of HA microparticles prepared at different crosslinking ratio, 2.5%, 5%, 10%, 25%, 50%, 100% using DVS as crosslinking agent based on the HA repeating unit.

| Materials | Surface area ($m^2/g$) | Pore volume ($cm^3/g$) | Pore size (nm) |
|---|---|---|---|
| 2.5% DVS | 21.54 ± 10.31 | 4.51 ± 2.78 | 8.3 ± 1.7 |
| 5% DVS | 14.33 ± 0.74 | 7.92 ± 1.40 | 8.2 ± 0.8 |
| 10% DVS | 0.32 ± 0.27 | 0.86 ± 0.16 | 5.4 ± 2.6 |
| 25% DVS | 0.00 ± 0.00 | 0.00 ± 0.00 | 0.0 ± 0.00 |
| 50% DVS | 0.00 ± 0.00 | 0.00 ± 0.00 | 0.0 ± 0.00 |
| 100% DVS | 0.00 ± 0.00 | 0.00 ± 0.00 | 0.0 ± 0.00 |

It is apparent from Table 3 that, the lower the crosslinking density, the higher the pore parameters such as surface area, pore volume and pore sizes. As the crosslinker ratio is increased to 20% or above HA particles become non-porous.

Hydrolytic Degradation of HA Microparticles

The hydrolytic degradation of HA microparticles that are prepared by using DVS as crosslinker at mole ratios (e.g., 2.5%, 5%, 10%, 25%, 50%, 100%) mole ratio of HA repeating unit was done at pH 7.4 at 37.5° C. For this purpose, 0.05 g of dried particles were placed in 50 mL of pH 7.4 buffer solutions at 37.5° C. with three replicates in a water shaker-bath under constant agitation. The degradation of HA particles (weight loss % of particles) was monitored for 30 days by collecting 0.5 mL of supernatant solution every second day and diluting with the corresponding buffer solution to 1.5 mL. All the experiments were performed in three replicates and the amount of degrading HA from the Ha particles were determined via HPLC using Thermo Ultimate 3000 HPLC system with refractive index (RI) detector containing rezex RNM-Carbohydrate Nae column (5 μm, 300 mm×7.8 mm) of phenomenex via the following conditions: 0.8 mL/min flow rate, 65° C. temperature of column and 35° C. temperature of RI detector, 20 μL of injection volume for 10 min run time. Sulfuric acid solution (5 mM) was used as the mobile phase. For the calibrations of hyaluronic acid, the standard buffer solutions (eight different concentrations) were prepared in PBS solution at pH 7.4.

Figure 10A:
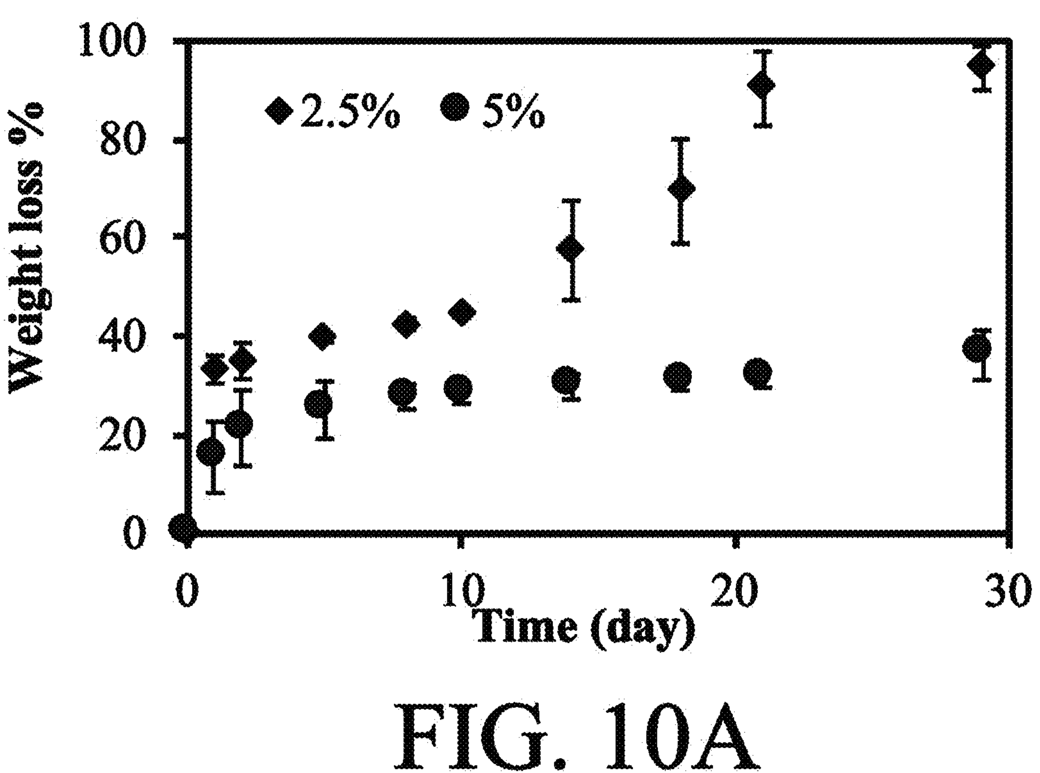
FIG. 10*a* depicts a graphical representation of weight loss (%) of HA particles crosslinked with DVS at different crosslinker ratios at 2.5 and 5 percent mole ratio relative to HA repeating unit.
Figure 10B:
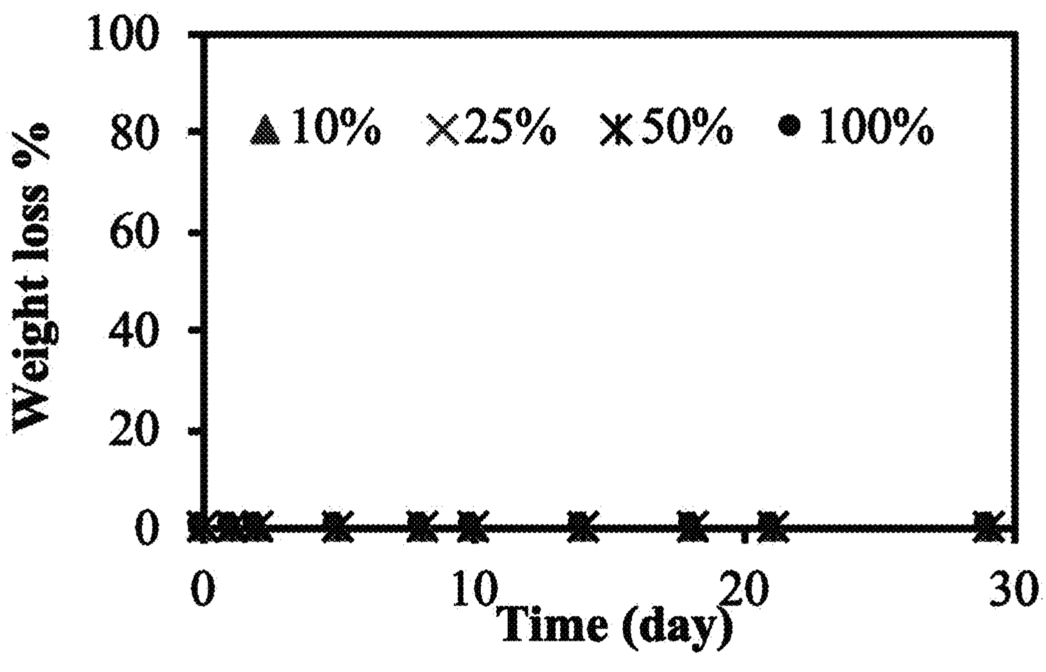
FIG. 10*b* depicts a graphical representation of weight loss (%) of HA particles crosslinked with DVS at different crosslinker ratios at 10, 25, 50, and 100 percent mole ratio relative to HA repeating unit.

The degradation profile with time is given in FIGS. 10*a* and 10*b*. Specifically, FIG. 10*a* depicts weight loss (%) of HA particles crosslinked with DVS at different crosslinker ratios (2.5% and 5%), and FIG. 10*b* depicts weight loss (%) of HA particles crosslinked with DVS at different cross-linker ratios of 10, 25, 50, and 100 mole ratio of HA repeating unit. FIGS. 10*a* and 10*b* clearly reveal that up to 30 days degradation time in PBS at pH 7.4 at 37.5° C., HA particles prepared by using more 10% DVS crosslinking do not degrade whereas only about 35% of HA particle were found to degrade for 5% DVS crosslinked HA particles. On the other hand, HA particles prepared by using 2.5% DVS degrades almost linearly after 3 days.

Preparing HA Particles Using Higher Amounts of DVS (>25 Mole % of HA Repeating Unit) in Presence of Porogen To prepare porous HA nanoparticles with higher amounts of DVS (>25%) poly vinyl pyrrolidone (PVP) was used as porogen. PVP, 25% and 50% weight ratio of HA as a pore making agent (porogen) was used for HA particles that are prepared with DVS at 50 and 100% mole ratio of HA repeating unit. The PVP solution in DI water is prepared by dissolving 150 mg PVP (MW: 40 000 g/mol) in 1 mL DI water (15 weight %) and different amounts of this solution as 0.050-0.100 mL is dispersed in 30 mL of 0.2 M AOT solution in isooctane. The HA solution is prepared by dissolving HA (MW:1000 KDa) in 0.2 M NaOH at a concentration of 30 mg/mL (3 wt % HA) and 1 mL of this HA solution was added in 30 mL of 0.2 M AOT solution in isooctane under constant mixing at 1000 rpm. After 5 min, DVS as a crosslinker at different mole ratios e.g., 50, 100 mole % relative to the HA repeating unit were added to the mixtures, and then whole mixture was vortexed again to make homogenous dispersion. The reactions were allowed to proceed for 1 h at ambient temperature with vigorous stirring (1,000 rpm). Then, the obtained HA nanoparticles were precipitated by centrifugation at 10,000 rpm for 10 min at 20° C. This was followed by removal of the supernatant solution and dispersal with ethanol and was followed by removal of the supernatant solution and re-dispersal with acetone and water mixture and centrifugation at least five times. The prepared particles were swollen in DI water, dried with a freeze-dry and kept in a closed container for further use.

TABLE 4

Surface area, pore volume, and pore size of HA microparticles prepared with different crosslinking ratio of DVS as 50%, 100% and porous (P-) HA microparticles prepared with two concentration of polyvinylpyrolydone (PVP) (25% and 50% weight ratio of HA) which are crosslinked with DVS at 50% mole ratio of HA.

| Materials | Surface area ($m^2/g$) | Pore volume (cm3/g) | Pore size (nm) |
|---|---|---|---|
| HA particles (50% DVS) | 0.00 ± 0.00 | 0.00 ± 0.00 | 0.0 ± 0.00 |
| HA particles (100% DVS) | 0.00 ± 0.00 | 0.00 ± 0.00 | 0.0 ± 0.00 |
| P-HA (25% PVP, 50% DVS) | 21.47 ± 9.12 | 11.15 ± 2.11 | 8.4 ± 2.3 |
| P-HA (50% PVP, 50% DVS) | 1.61 ± 0.95 | 8.47 ± 1.06 | 12.8 ± 1.6 |
| P-HA (25% PVP, 100% DVS) | 8.71 ± 2.33 | 13.29 ± 4.85 | 7.6 ± 1.9 |
| P-HA (50% PVP, 100% DVS) | 0.014 ± 0.01 | 1.07 ± 0.94 | 9.9 ± 2.7 |

It obvious from Table 4, the even non-porous HA particle with >25% mole DVS crosslinked can be made porous by using different and amounts of porogen materials such as PVP. The amounts and the MW of PVP (10 000-1 300 000) can varied to obtained HA particles with different porosity. Table 4 shows the BET analysis results of HA particles prepared with different amount of DVS crosslinker.

Experiment 5: Modification of HA Particles for Enhanced Functionality

Methods

For modification of HA nanoparticles, 200 μL of trimethylolpropane triglycidyl ether (TMPGDE) was placed in 5 mL of 0.2 M NaOH solution under 500 rpm mixing rate at room temperature. After 30 min, 200 mg of porous-HA (P-HA) particles was suspended into this mixture and reacted for 1 h more. These particles denoted as modified-HA (M-HA) particles was then precipitated in excess amount of ethanol and the particles was washed ethanol by centrifugation at 10,000 rpm for 10 min at 20° C. at least three times. M-P-HA nanoparticles was dried with heat gun and kept in a closed container for further use.

Upon modification, the number —OH functional groups on P-HA particle can be significantly increased. And these functional groups can increase the active agent, such as drugs, hormones, growth factor, peptide and proteins, etc., conjugation or attachments capabilities for delivery device applications. To corroborate the modification reaction, the Fourier Transform Infrared Radiation (FT-IR) spectra of HA particle before modification, (Porous-Hyaluronic Acid (P-HA)) and after modification (Modified-Porous-Hyaluronic acid (M-P-HA)) with TMPGDE was recorded and shown in FIG. 11.

Figure 11:
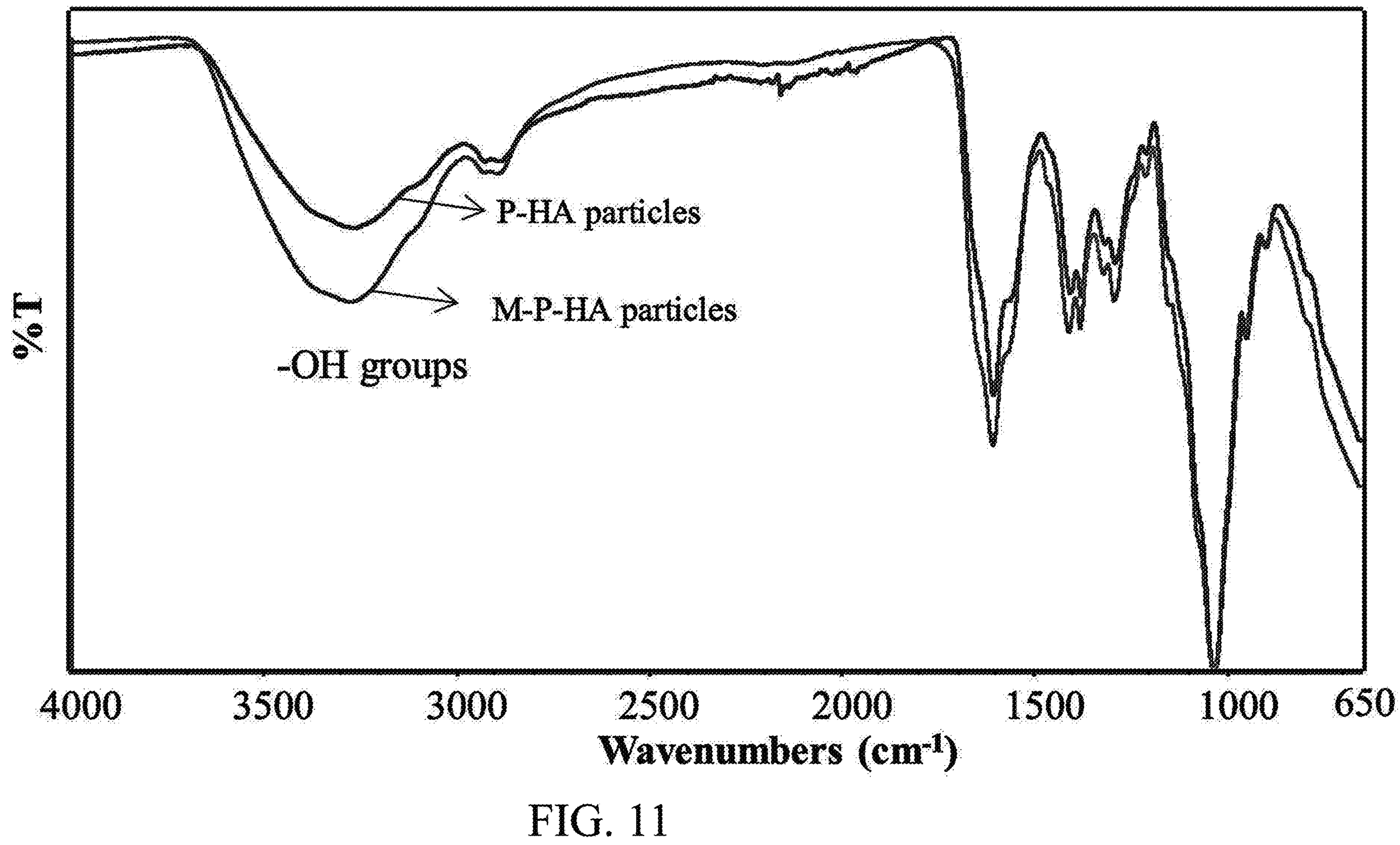
FIG. 11 depicts a graphical representation of the FT-IR spectra of Porous-HA (P-HA) and Modified-Porous-HA (M-P-HA) nanoparticles.

It is apparent from FIG. 11 that the intensity of the stretching frequency of —OH functional groups between 3000-3500 $cm^{-1}$ is significantly increased. Furthermore, the zeta potential measurements also further confirm the increase of the surface functionality upon TMPGDE modification of the HA particles. The zeta potential measurements of HA based particles are given in Table 5.

TABLE 5

Zeta potential measurement (mV) bare, porous (P-) and modified porous (M-P-) HA microparticles.

| Materials | Zeta Potential (mV) |
|---|---|
| HA microparticles | −28.12 ± 2.54 |
| P-HA microparticles | −17.39 ± 1.31 |
| M-P-HA microparticles | −27.91 ± 1.27 |

As the zeta potential is directly related to the surface functionality of the particles, the increase of zeta potential from about 17 to about −27 mV clearly confirms the increase in the number of —OH functionality of HA particles. As non-porous HA particle possess about −28 mV seems higher than p-HA and M-P-HA particles also evidently shows that with the pore formation on particle surface some of the functionality embedded within the pores of the particles. Other modification agents such 3-Chloro-2-hydroxy-1-propanesulfonic acid to introduce —$SO_3H$ functionality, and 3-Chloropropylamine to introduce —$NH_2$ functionality, 4-bromo butyronitrile to introduce –CN functionality, bromoacetic acid to introduce —COOH functionality, and bromo- or chloro-alkanes with different alkyl chain lengths such as $Br(CH_2)_nCH_3$ where n can be 1 to 17 can be readily used to modify HA and porous HA particles to render different physicochemical characteristics.

Ciprofloxacin Loading and Conjugation to Porous HA Particles

For conjugation (C) of HA particles with Ciprofloxacin, three crosslinker ratio of HA particles (2.5, 5, and 10% DVS) were used. In brief, 0.1266 g of Ciprofloxacin were dissolved in 10 mL dimethyl sulfoxide (DMSO), then, 0.068 g of 1,1'-carbonyldiimidazole was added to this solution and stirred at room temperature for 1 h. Subsequently, 0.2 g HA particles was added to the drug mixture and the reaction was allowed to react for 24 h at 80° C. under stirring. The conjugated HA particles was washed with DMSO one time and washed with acetone two times and dried in a freeze dryer.

For physical drug loading process (adsorption), 0.15 g dried HA particles was placed into 20 mL of DMSO solution containing 0.1 g Ciprofloxacin and stirred at room temperature. The particles were washed with DMSO one time and washed with acetone two times and dried with freeze drier.

In the Ciprofloxacin release studies, 50 mg of drug conjugated (C) and adsorbed (A) HA particles were dispersed in 1 mL of PBS at pH 7.4 and transferred to a dialysis membrane. The drug loaded particle containing membrane was put into 50 mL of PBS (pH 7.4) at 37.5° C. in a shaker bath. The drug containing solution in PBS was then taken and absorbance value at 270 nm in UV-Vis spectrometer was measured, and the released amount of Ciprofloxacin was determined from a previously determined drug calibration curve. The analysis was repeated for three times and depicted in FIG. 12, which shows the Ciprofloxacin release profile from Ciprofloxacin absorbed (A) and conjugated (C) HA microgels crosslinked with DVS at different crosslinker ratios at pH 7.4 in PBS at 37.5° C.

Figure 12:
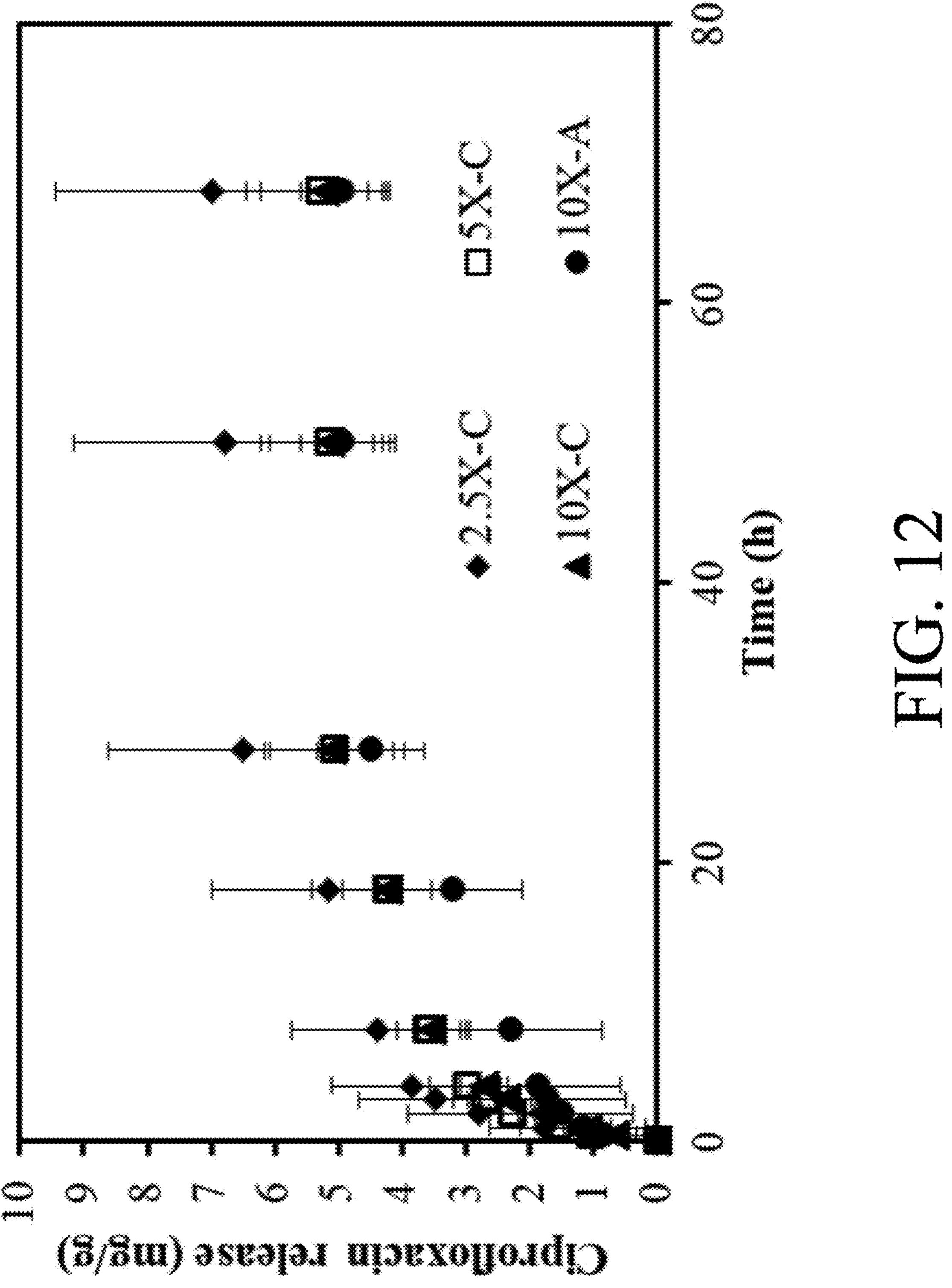
FIG. 12 depicts a graphical representation of a Ciprofloxacin release profile from Ciprofloxacin absorbed (A) and conjugated (C) HA microgels crosslinked with DVS at different crosslinker ratios at pH 7.4 in PBS at 37.5° C.

As can be seen from FIG. 12, the amounts of Ciprofloxacin release for porous HA particles depend on the pore structure, e.g., 2.5% DVS crosslinked HA particles have higher porosity and release higher amounts of drugs in comparison to 5 and 10% DVS crosslinked HA particles.

Vancomycin Loading and Conjugation Processes to Porous HA Particles

For Vancomycin conjugation (C) of HA particles, HA particles prepared by three crosslinker ratio e.g., 2.5, 5, and 10% DVS were used. In short, 0.1 g of Vancomycin were dissolved in 10 mL DMSO solution. Then, 0.068 g of 1,1'-carbonyldiimidazole was added to this solution and stirred at room temperature for 1 h. Subsequently, 0.2 g HA particles was added to the drug mixture and the reaction was allowed to react for 24 h at 80° C. under stirring. The Vancomycin conjugated HA particles were washed with DMSO one time and washed with acetone two times and dried with freeze drier.

For physical drug loading process (adsorption-A), 0.15 g dried HA particles was put into 20 mL of DMSO solution containing 0.1 g Vancomycin and stirred at room temperature. The particles were washed with DMSO one time and washed with acetone two times and dried with freeze drier.

For Vancomycin release studies, 50 mg of Vancomycin conjugated (C) and physically adsorbed (A) HA particles were dispersed in 1 mL of PBS at pH 7.4 and transferred to a dialysis membrane. Then this membrane was placed into 50 mL of PBS (pH 7.4) at 37.5° C. in a shaker bath. The drug containing solution in PBS was then sampled and the absorbance values was read via UV-Vis spectrometer at 280 nm, and the released amount of Vancomycin was determined from a previously constructed calibration. All the analysis was repeated for three times.

Figure 13:
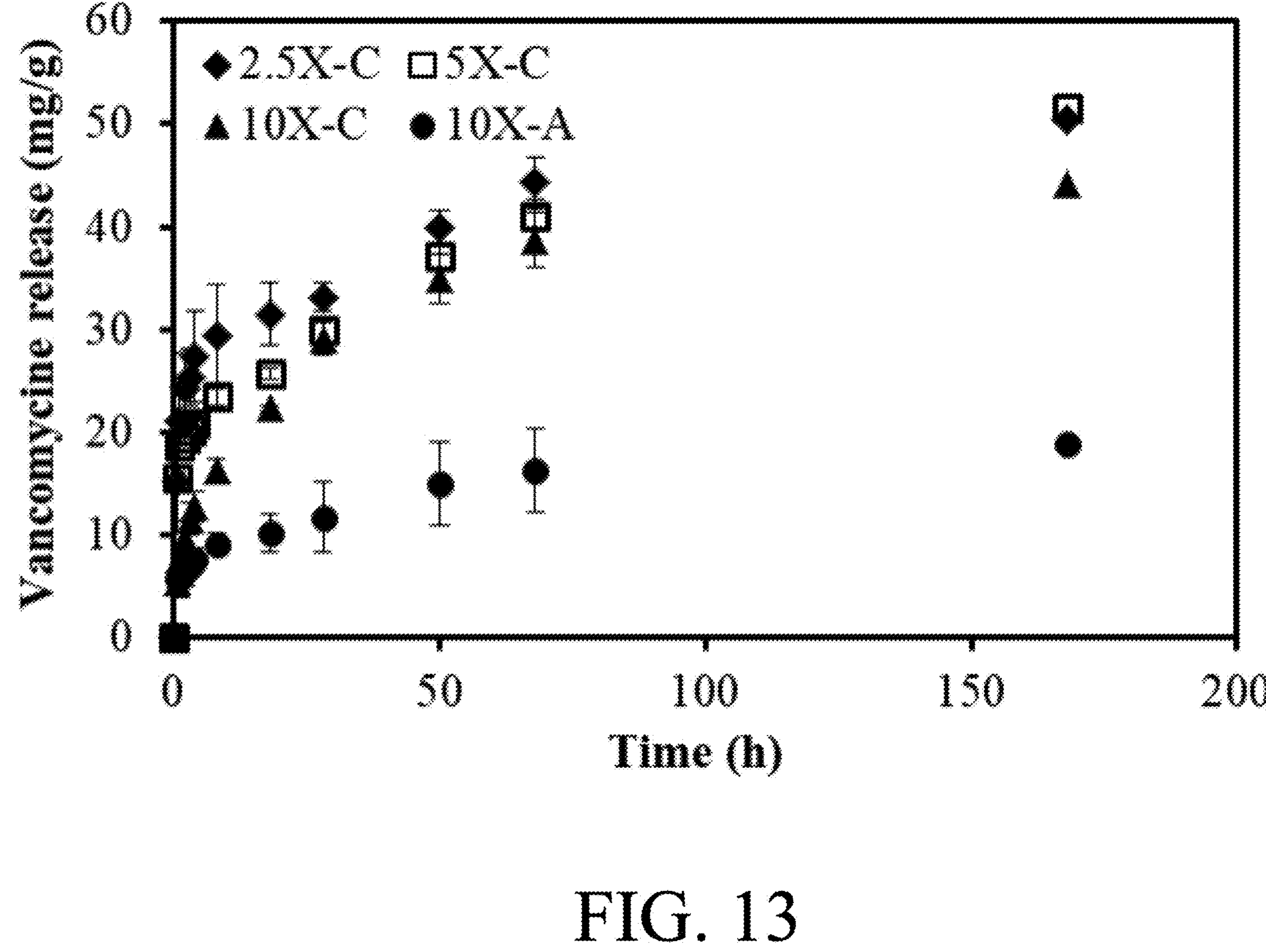
FIG. 13 depicts a graphical representation of a Vancomycin release profile from Vancomycin absorbed (A) and conjugated (C) HA particles crosslinked with DVS at different crosslinker ratios at pH 7.4 PBS at 37.5° C.

FIG. 13 demonstrates Vancomycin release profile of porous HA particles. As can be seen, the drug loading and release amount can be readily controlled by porosity of HA particles and the drug loading procedure. For example, 2.5 and 5% DVS crosslinked particles (loaded by conjugation) can release higher amounts of Vancomycin (up to 50 mg/g) for about 7 days whereas 10% DVS crosslinked particles (loaded by conjugation) release about 40 mg/g Vancomycin in about 7 days. Specifically, FIG. 13 depicts a Vancomycin release profile from Vancomycin absorbed (A) and conjugated (C) HA particles crosslinked with DVS at different crosslinker ratios at pH 7.4 in PBS at 37.5° C.

On the other hand, by using physically adsorbed drug loading process (A) into 10% DVS crosslinked HA particles, the release amount is significantly reduced, e.g., 20 mg/g in seven days. Therefore, the by choice of drug loading e.g., physical adsorption and chemical crosslinking and with the appropriate choice of porous HA particles, the release kinetic of active agent can be controlled in terms of amounts and time.

Anti-Fibrotic and Anti-Cancer Drug Loading into Porous HA Based Particles (Modified and Unmodified Porous HA Particles)

Porous HA particles and modified forms of porous HA particles can be loaded with some cancer medications such as Mitomycin C (MMC), 5-Fluorouacil (5-FU) and Cisplatin (CP). The loading of these drugs into HA based porous particles can be accomplished by means of physical adsorption where the interactions between the HA based particles and drugs can be hydrophilic interactions, hydrophobic interaction, dipole-dipole interaction or electrostatic interactions. As porous HA particles have higher surface area and higher porosity in comparison to non-porous HA particles, more drug molecules can be loaded into their porous network structure.

Predetermined amounts of drugs, MMC, 5-FU and CP etc. are dissolved in a suitable solvent such as DI water, methanol, ethanol, Dimethyl formamide (DMF), Dimethyl sulfoxide (DMSO) as is known the art to bring drugs into solution, and predetermined amount of porous HA particles or modified porous HA are then placed into one of these drug solutions (such as by soaking) under constant mixing between 100-1,000 rpm at room temperature in the dark. Depending on the extents of the porosity and the types of the functional groups that are generated on the modified porous HA particles, different amounts of drug molecule can be embedded within the porous of HA (or modified porous HA) particles. The interstices of porous HA polymeric chains can be filled with the desired amount of drug molecules with the desired drug types by the appropriate choice porosity of porous HA particles, the types of the used modifying and the choice of used solvent to imbibe the drug molecules into HA based porous particles. Depending on the concentration of the drugs within the pores of HA particles, the drug delivery systems can be used for different purpose, for example for MMC.

Different dosages of drugs can be loaded for different purposes. For example, anti-fibrotic low dose MMC can prevent scare tissue formation after glaucoma surgery, and to treat cancer high dose MMC can be used to target and kill cancer cells within the various parts of the body.

Interferons and Insulin Delivery with Porous HA and Modified Porous HA Particle

Porous HA and modified porous HA particles can also be used as carriers for delivering interferons and insulin to various parts of human body including human eyes. HA based particles can be loaded at desired amounts with interferons and insulin by placing dried HA based particles into the corresponding drug solutions in distilled water or phosphate buffer saline solution (PBS) or balanced salt solution or appropriate organic solvent. After centrifugation for separation of interferons and/or insulin loaded HA based particles, these drug loaded HA based particles can be used to prepare appropriate injectable formulations in water, PBS, or BBS. Furthermore, these drugs, such as interferons and insulin, can be chemically linked to HA based particles for the purpose of prolonged delivery into various parts of body, as these drugs have many functional groups such as —$NH_2$, —COOH and —OH and —SH.

While the invention has been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

What is claimed is:

1. A biologically active rapid release therapeutic agent polymer composition comprising:

a hyaluronic acid (HA) polymer formed of HA particles, the HA particles comprising HA repeating units;

a therapeutic agent covalently bound to the HA polymer; and, a crosslinking agent present at less than 20% mole relative to the HA repeating units;

wherein the HA particles are porous HA particles formed by crosslinking at said less than 20% mole amount by dispersing an aqueous HA solution in a sodium bis(2-ethylhexyl) sulfosuccinate (AOT) solution in isooctane, the porous HA particles having an average surface area between 0.32 m2/g and 21.54 m2/g, an average pore volume of between 0.86 cm3/g and 7.92 cm3/g, and an average pore size between 5.4 nm and 8.3 nm;

wherein the HA polymer is adapted to release the therapeutic agent to achieve a therapeutic range within approximately 24 hours after administration; and wherein the therapeutic agent is substantially released from the HA-polymer within 80-120 hours after administration.

2. The composition of claim 1 wherein the therapeutic agent is an antibiotic and wherein the therapeutic agent is substantially released from the HA polymer within 80-120 hours after administration, and wherein the AOT solution is a 0.2M AOT solution used during synthesis in isooctane, wherein the HA polymer is adapted to release the antibiotic to achieve a therapeutic range within approximately 24 hours after administration.

3. The composition of claim 2, wherein the crosslinking agent is divinyl sulfone (DVS).

4. The composition of claim 3, wherein the amount of crosslinking agent is present at less than 10% mole relative to the HA repeating units.

5. The composition of claim 3, wherein the amount of crosslinking agent is present at less than 5% mole relative to the HA repeating units.

6. The composition of claim 3, wherein the amount of crosslinking agent is present at less than 2.5% mole relative to the HA repeating units.

7. The composition of claim 2, wherein the HA polymer further includes a simple carbohydrate conjugated to the HA-polymer, wherein the HA polymer is an HA-carbohydrate-antibiotic polymer, whereby the simple carbohydrate attracts bacteria to proximate of the antibiotic.

8. The composition of claim 7, wherein the simple carbohydrate is sucrose.

9. The composition of claim 8, wherein the HA repeating units are modified HA repeating units having at least one of modified functional groups of —OH, —$NH_2$, —COOH, —SH, —$SO_3H$, and —CN, thereby increasing conjugation sites on the HA polymer for the therapeutic agent.

10. The composition of claim 1, wherein the therapeutic agent is selected from the group consisting of Mitomycin C, 5-Fluorouacil and Cisplatin.

11. The composition of claim 1, wherein the therapeutic agent is selected from the group consisting of interferons and insulin.

* * * * *